(12) United States Patent
Liao et al.

(10) Patent No.: US 7,700,319 B2
(45) Date of Patent: Apr. 20, 2010

(54) PRODUCTION OF 3-HYDROXYPROPIONIC ACID USING BETA-ALANINE/PYRUVATE AMINOTRANSFERASE

(75) Inventors: Hans H. Liao, Eden Prairie, MN (US); Ravi R. Gokarn, Minneapolis, MN (US); Steven John Gort, Brooklyn Center, MN (US); Holly Jean Jessen, Chanhassen, MN (US); Olga V. Selifonova, Plymouth, MN (US)

(73) Assignee: Novozymes A/S, Bagsvaerd (DK)

( * ) Notice: Subject to any disclaimer, the term of this patent is extended or adjusted under 35 U.S.C. 154(b) by 422 days.

(21) Appl. No.: 10/581,570

(22) PCT Filed: Dec. 6, 2004

(86) PCT No.: PCT/US2004/040827

§ 371 (c)(1),
(2), (4) Date: Jun. 2, 2006

(87) PCT Pub. No.: WO2005/118719

PCT Pub. Date: Dec. 15, 2005

(65) Prior Publication Data

US 2007/0107080 A1 May 10, 2007

Related U.S. Application Data

(60) Provisional application No. 60/527,357, filed on Dec. 4, 2003.

(51) Int. Cl.
*A01H 1/00* (2006.01)
*C07H 21/04* (2006.01)
*C12P 7/64* (2006.01)
*C12P 7/62* (2006.01)

(52) U.S. Cl. .................. 435/69.1; 435/193; 435/252.3; 435/252.33; 435/419; 435/134; 800/281

(58) Field of Classification Search .................. None
See application file for complete search history.

(56) References Cited

U.S. PATENT DOCUMENTS 7,186,541 B2 * 3/2007 Gokarn et al. .............. 435/232

FOREIGN PATENT DOCUMENTS

| WO | WO 01/16346 A1 | 3/2001 |
| WO | WO 02/42418 A2 | 5/2002 |
| WO | WO 03/062173 A2 | 7/2003 |

OTHER PUBLICATIONS

Beta-alanine as an Ethylene Precursor. Investigation Towards Preparation and Properties, of a Soluble Enzyme System from a Subcellular Particulate Function of Bean Cotyledons.Stinton et al. Plant Physiology (1969) 44,1217-1226.*
Database UniProt Accession No. P28269 (Dec. 1, 1992).
Database UniProt Accession No. Q88Q98 (Jun. 1, 2003).
Database UniProt Accession No. Q889H5 (Jun. 1, 2003).
Accession No. P28269 (Jun. 15, 2002).
Accession No. NP_114023 (Nov. 13, 2003).
Yonaha et al., "Properties of the Bound Coenzyme and Subunit Structure of ω-Amino Acid:Pyruvate Aminotransferase," *J. Biol. Chem.* 258:2260-2265 (1983).
Yonaha et al., "The Primary Structure of ω-Amino Acid:Pyruvate Aminotransferase," *J. Biol. Chem.* 267:12506-12510 (1992).

* cited by examiner

*Primary Examiner*—Manjunath N Rao
*Assistant Examiner*—Kagnew H Gebreyesus
(74) *Attorney, Agent, or Firm*—Klarquist Sparkman, LLP

(57) ABSTRACT

Methods of using beta-alanine/pyruvate aminotransferase to produce 3-hydroxypropionic acid and derivatives thereof, from beta-alanine, are disclosed. Cells and recombinant nucleic acids that can be used to practice the methods are also disclosed.

38 Claims, 1 Drawing Sheet

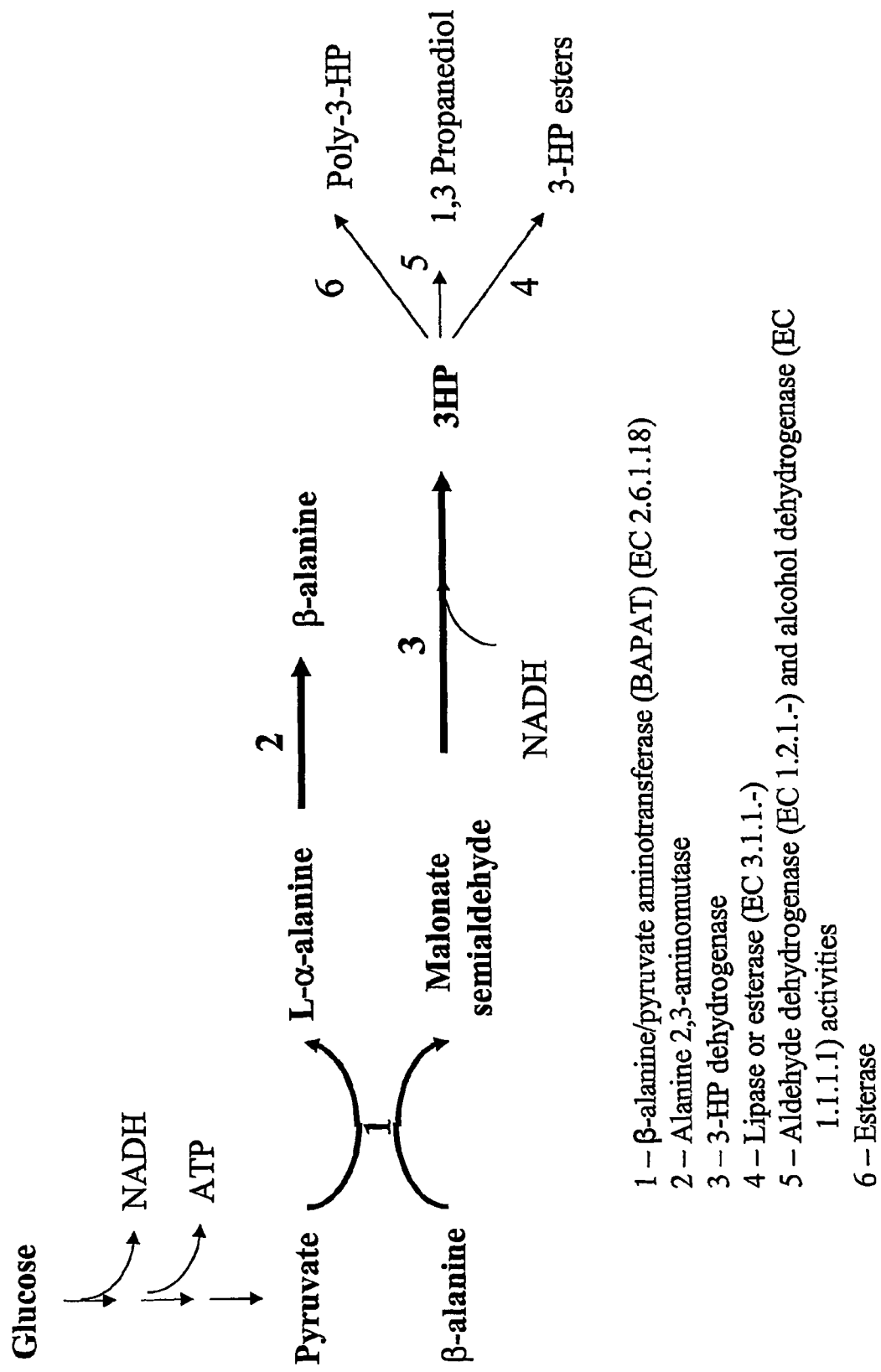

SEQUENCE LISTING

<160> NUMBER OF SEQ ID NOS: 28

<210> SEQ ID NO 1
<211> LENGTH: 60
<212> TYPE: DNA
<213> ORGANISM: Artificial
<220> FEATURE:
<223> OTHER INFORMATION: PCR primer

<400> SEQUENCE: 1
atatttttag tagcttaaat gtgattcaac atcactggag gtgtaggctg gagctgcttc        60

<210> SEQ ID NO 2
<211> LENGTH: 60
<212> TYPE: DNA
<213> ORGANISM: Artificial
<220> FEATURE:
<223> OTHER INFORMATION: PCR primer

<400> SEQUENCE: 2
tatctgaatc agctcccctg gaatgcaggg gagcggcaag catatgaata tcctccttag        60

<210> SEQ ID NO 3
<211> LENGTH: 22
<212> TYPE: DNA
<213> ORGANISM: Artificial
<220> FEATURE:
<223> OTHER INFORMATION: PCR primer

<400> SEQUENCE: 3
ttcaatatcg ccatagcttt ca        22

<210> SEQ ID NO 4
<211> LENGTH: 19
<212> TYPE: DNA
<213> ORGANISM: Artificial
<220> FEATURE:
<223> OTHER INFORMATION: PCR primer

<400> SEQUENCE: 4
gaggatgaaa ggtcattgg        19

<210> SEQ ID NO 5
<211> LENGTH: 33
<212> TYPE: DNA
<213> ORGANISM: Artificial
<220> FEATURE:
<223> OTHER INFORMATION: PCR primer

<400> SEQUENCE: 5
aagcccgagg atcgacatat gaaccagccg ctc                                    33

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
ccacctgcac ggtgggtacg gc                                                22

<210> SEQ ID NO 7
<211> LENGTH: 35
<212> TYPE: DNA
<213> ORGANISM: Artificial
<220> FEATURE:
<223> OTHER INFORMATION: PCR primer

<400> SEQUENCE: 7
tcttccgagg aaccgcatat gaacatgccc gaaac                                  35

<210> SEQ ID NO 8
<211> LENGTH: 41
<212> TYPE: DNA
<213> ORGANISM: Artificial
<220> FEATURE:
<223> OTHER INFORMATION: PCR primer

<400> SEQUENCE: 8
gcatacgcct ggcattaatt aaggaaagat cagtcgatca g                           41

<210> SEQ ID NO 9
<211> LENGTH: 27
<212> TYPE: DNA
<213> ORGANISM: Artificial
<220> FEATURE:
<223> OTHER INFORMATION: PCR primer

<400> SEQUENCE: 9
atacatatga ccgacatcgc attcctc                                           27

<210> SEQ ID NO 10
<211> LENGTH: 28
<212> TYPE: DNA
<213> ORGANISM: Artificial
<220> FEATURE:
<223> OTHER INFORMATION: PCR primer

<400> SEQUENCE: 10
atagtcgact tagggatgaa gcagtgag                                          28

<210> SEQ ID NO 11
<211> LENGTH: 64
<212> TYPE: DNA
<213> ORGANISM: Artificial
<220> FEATURE:
<223> OTHER INFORMATION: PCR primer

```
<220> FEATURE:
<221> NAME/KEY: misc_feature
<222> LOCATION: (46)..(46)
<223> OTHER INFORMATION: S at position 46 is a g or c

<400> SEQUENCE: 11
caacggcatc gcctaatgaa cggccgctta attaagaagg aggtastaaa tatgaccgac    60
atcg                                                                64

<210> SEQ ID NO 12
<211> LENGTH: 46
<212> TYPE: DNA
<213> ORGANISM: Artificial
<220> FEATURE:
<223> OTHER INFORMATION: PCR primer

<400> SEQUENCE: 12
ttcgttttat ttgatgcctc tagattagtc cttgccgcgg tagagc                  46

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
gagcaatcac ctatgaactg                                               20

<210> SEQ ID NO 14
<211> LENGTH: 75
<212> TYPE: DNA
<213> ORGANISM: Artificial
<220> FEATURE:
<223> OTHER INFORMATION: PCR primer

<400> SEQUENCE: 14
gagcggctgg ttcatttgta ccttcctcct ctttaatggc ggccgcacca ttcgcatgtt    60
tttatgaaga atccc                                                    75

<210> SEQ ID NO 15
<211> LENGTH: 47
<212> TYPE: DNA
<213> ORGANISM: Artificial
<220> FEATURE:
<223> OTHER INFORMATION: PCR primer

<400> SEQUENCE: 15
cacacagaat gcggccgcga ggagaaaggt aaatatgaac atgcccg                 47

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
cgttcaccga caaacaacag                                               20

<210> SEQ ID NO 17
<211> LENGTH: 1347
<212> TYPE: DNA
<213> ORGANISM: Pseudomonas putida
```

```
<220> FEATURE:
<221> NAME/KEY: CDS
<222> LOCATION: (1)..(1344)

<400> SEQUENCE: 17 atg aac atg ccc gaa act ggt cct gcc ggt atc gcc agc cag ctc aag        48
Met Asn Met Pro Glu Thr Gly Pro Ala Gly Ile Ala Ser Gln Leu Lys
1               5                   10                  15 ctg gac gcc cac tgg atg ccc tac acc gcc aac cgc aac ttc cag cgc        96
Leu Asp Ala His Trp Met Pro Tyr Thr Ala Asn Arg Asn Phe Gln Arg
            20                  25                  30 gac cca cgc ctg atc gtg gcg gcc gaa ggc aac tac ctg gtc gat gac       144
Asp Pro Arg Leu Ile Val Ala Ala Glu Gly Asn Tyr Leu Val Asp Asp
        35                  40                  45 cac ggg cgc aag atc ttc gac gcc ctg tcc ggc ctg tgg acc tgc ggc       192
His Gly Arg Lys Ile Phe Asp Ala Leu Ser Gly Leu Trp Thr Cys Gly
    50                  55                  60 gca ggg cac act cgc aag gaa atc gct gac gcg gtg acc cgt caa ctg       240
Ala Gly His Thr Arg Lys Glu Ile Ala Asp Ala Val Thr Arg Gln Leu
65                  70                  75                  80 agt acg ctg gac tac tcc cca gcg ttc cag ttc ggc cac ccg ctg tcg       288
Ser Thr Leu Asp Tyr Ser Pro Ala Phe Gln Phe Gly His Pro Leu Ser
                85                  90                  95 ttc cag ctg gcg gaa aag atc gcc gag ctg gtt ccg ggc aat ctg aat       336
Phe Gln Leu Ala Glu Lys Ile Ala Glu Leu Val Pro Gly Asn Leu Asn
            100                 105                 110 cac gtc ttc tat acc aac tcc ggt tcc gag tgc gcc gat acc gca ctg       384
His Val Phe Tyr Thr Asn Ser Gly Ser Glu Cys Ala Asp Thr Ala Leu
        115                 120                 125 aag atg gtg cgt gcc tac tgg cgc ctg aaa ggc cag gca acc aag acc       432
Lys Met Val Arg Ala Tyr Trp Arg Leu Lys Gly Gln Ala Thr Lys Thr
    130                 135                 140 aag atc atc ggc cgt gcc cgt ggt tac cat ggc gtg aac atc gcc ggt       480
Lys Ile Ile Gly Arg Ala Arg Gly Tyr His Gly Val Asn Ile Ala Gly
145                 150                 155                 160 acc agc ctg ggt ggc gtc aac ggt aac cgc aag atg ttt ggc cag ctg       528
Thr Ser Leu Gly Gly Val Asn Gly Asn Arg Lys Met Phe Gly Gln Leu
                165                 170                 175 ctg gac gtc gac cac ctg cct cac act gta ttg ccg gtg aac gcc ttc       576
Leu Asp Val Asp His Leu Pro His Thr Val Leu Pro Val Asn Ala Phe
            180                 185                 190 tcg aaa ggc ttg ccg gaa gag ggc ggt atc gcg ctg gct gac gaa atg       624
Ser Lys Gly Leu Pro Glu Glu Gly Gly Ile Ala Leu Ala Asp Glu Met
        195                 200                 205 ctc aag ctg atc gag ctg cac gat gcc tcc aac atc gca gca gtc atc       672
Leu Lys Leu Ile Glu Leu His Asp Ala Ser Asn Ile Ala Ala Val Ile
    210                 215                 220 gtc gag ccg ctg gcc ggt tcg gcc ggt gtg ctg ccg ccg cca aag ggt       720
Val Glu Pro Leu Ala Gly Ser Ala Gly Val Leu Pro Pro Pro Lys Gly
225                 230                 235                 240 tac ctg aag cgc ctg cgt gaa atc tgc acc cag cac aac att ctg ctg       768
Tyr Leu Lys Arg Leu Arg Glu Ile Cys Thr Gln His Asn Ile Leu Leu
                245                 250                 255 atc ttc gac gaa gtg atc aca ggc ttc ggc cgc atg ggc gcg atg acc       816
Ile Phe Asp Glu Val Ile Thr Gly Phe Gly Arg Met Gly Ala Met Thr
            260                 265                 270 ggc tcg gaa gcc ttc ggc gtt acc ccg gac ctg atg tgc atc gcc aag       864
Gly Ser Glu Ala Phe Gly Val Thr Pro Asp Leu Met Cys Ile Ala Lys
        275                 280                 285
```

```
cag gtg acc aac ggc gcc atc ccg atg ggc gca gtg att gcc agc agc      912
Gln Val Thr Asn Gly Ala Ile Pro Met Gly Ala Val Ile Ala Ser Ser
    290                 295                 300 gag atc tac cag acc ttc atg aac cag ccg acc ccg gaa tac gcc gtg      960
Glu Ile Tyr Gln Thr Phe Met Asn Gln Pro Thr Pro Glu Tyr Ala Val
305                 310                 315                 320 gaa ttc cca cac ggc tac acc tat tcg gcg cac ccg gta gcc tgt gcc     1008
Glu Phe Pro His Gly Tyr Thr Tyr Ser Ala His Pro Val Ala Cys Ala
                325                 330                 335 gcc ggt ctc gcc gcg ctg gac ctg ctg cag aag gaa aac ctg gtg cag     1056
Ala Gly Leu Ala Ala Leu Asp Leu Leu Gln Lys Glu Asn Leu Val Gln
            340                 345                 350 tcc gcg gct gaa ctg gcg ccg cat ttc gag aag ctg ctg cac ggc gtg     1104
Ser Ala Ala Glu Leu Ala Pro His Phe Glu Lys Leu Leu His Gly Val
        355                 360                 365 aag ggc acc aag aat atc gtc gat atc cgc aac tac ggc ctg gcc ggc     1152
Lys Gly Thr Lys Asn Ile Val Asp Ile Arg Asn Tyr Gly Leu Ala Gly
370                 375                 380 gcc atc cag atc gcc gcc cgt gac ggt gat gcc atc gtt cgc cct tac     1200
Ala Ile Gln Ile Ala Ala Arg Asp Gly Asp Ala Ile Val Arg Pro Tyr
385                 390                 395                 400 gaa gcg gcc atg aag ctg tgg aaa gcg ggc ttc tat gta cgc ttt ggt     1248
Glu Ala Ala Met Lys Leu Trp Lys Ala Gly Phe Tyr Val Arg Phe Gly
                405                 410                 415 ggc gac acc ctg cag ttc ggc cca acc ttc aat acc aag ccg cag gaa     1296
Gly Asp Thr Leu Gln Phe Gly Pro Thr Phe Asn Thr Lys Pro Gln Glu
            420                 425                 430 ctg gac cgc ttg ttc gat gct gtt ggc gaa acc ctg aac ctg atc gac     1344
Leu Asp Arg Leu Phe Asp Ala Val Gly Glu Thr Leu Asn Leu Ile Asp
        435                 440                 445 tga                                                                  1347

<210> SEQ ID NO 18
<211> LENGTH: 448
<212> TYPE: PRT
<213> ORGANISM: Pseudomonas putida

<400> SEQUENCE: 18

Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160
```

```
Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Glu Gly Gly Ile Ala Leu Ala Asp Glu Met
        195                 200                 205

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
            260                 265                 270

Gly Ser Glu Ala Phe Gly Val Thr Pro Asp Leu Met Cys Ile Ala Lys
        275                 280                 285

Gln Val Thr Asn Gly Ala Ile Pro Met Gly Ala Val Ile Ala Ser Ser
    290                 295                 300

Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
                325                 330                 335

Ala Gly Leu Ala Ala Leu Asp Leu Leu Gln Lys Glu Asn Leu Val Gln
            340                 345                 350

Ser Ala Ala Glu Leu Ala Pro His Phe Glu Lys Leu Leu His Gly Val
        355                 360                 365

Lys Gly Thr Lys Asn Ile Val Asp Ile Arg Asn Tyr Gly Leu Ala Gly
    370                 375                 380

Ala Ile Gln Ile Ala Ala Arg Asp Gly Asp Ala Ile Val Arg Pro Tyr
385                 390                 395                 400

Glu Ala Ala Met Lys Leu Trp Lys Ala Gly Phe Tyr Val Arg Phe Gly
                405                 410                 415

Gly Asp Thr Leu Gln Phe Gly Pro Thr Phe Asn Thr Lys Pro Gln Glu
            420                 425                 430

Leu Asp Arg Leu Phe Asp Ala Val Gly Glu Thr Leu Asn Leu Ile Asp
        435                 440                 445

<210> SEQ ID NO 19
<211> LENGTH: 1347
<212> TYPE: DNA
<213> ORGANISM: Pseudomonas aeruginosa
<220> FEATURE:
<221> NAME/KEY: CDS
<222> LOCATION: (1)..(1344)

<400> SEQUENCE: 19 atg aac cag ccg ctc aac gtg gcc ccg ccg gtt tcc agc gaa ctc aac      48
Met Asn Gln Pro Leu Asn Val Ala Pro Pro Val Ser Ser Glu Leu Asn
1               5                   10                  15 ctg cgc gcc cac tgg atg ccc ttc tcc gcc aac cgc aac ttc cag aag      96
Leu Arg Ala His Trp Met Pro Phe Ser Ala Asn Arg Asn Phe Gln Lys
            20                  25                  30 gac ccg cgg atc atc gtc gcc gcc gaa ggc agc tgg ctg acc gac gac     144
Asp Pro Arg Ile Ile Val Ala Ala Glu Gly Ser Trp Leu Thr Asp Asp
        35                  40                  45
```

```
aag ggc cgc aag gtc tac gac agc ctg tcc ggc ctg tgg acc tgc ggc    192
Lys Gly Arg Lys Val Tyr Asp Ser Leu Ser Gly Leu Trp Thr Cys Gly
 50                  55                  60 gcc ggc cac tcg cgc aag gaa atc cag gag gcg gtg gct cgc cag ctc    240
Ala Gly His Ser Arg Lys Glu Ile Gln Glu Ala Val Ala Arg Gln Leu
 65                  70                  75                  80 ggc acc ctc gac tac tcg ccg ggc ttc cag tac ggc cat ccg ctg tcc    288
Gly Thr Leu Asp Tyr Ser Pro Gly Phe Gln Tyr Gly His Pro Leu Ser
                 85                  90                  95 ttc cag ttg gcc gag aag atc gcc ggg ttg ctg cca ggc gaa ctg aac    336
Phe Gln Leu Ala Glu Lys Ile Ala Gly Leu Leu Pro Gly Glu Leu Asn
            100                 105                 110 cac gtg ttc ttc acc ggt tcc ggc tcc gag tgc gcc gac acc tcg atc    384
His Val Phe Phe Thr Gly Ser Gly Ser Glu Cys Ala Asp Thr Ser Ile
        115                 120                 125 aag atg gcc cgc gcc tac tgg cgc ctg aaa ggc cag ccg cag aag acc    432
Lys Met Ala Arg Ala Tyr Trp Arg Leu Lys Gly Gln Pro Gln Lys Thr
130                 135                 140 aag ctg atc ggc cgc gcc cgc ggc tac cac ggg gtc aac gtc gcc ggc    480
Lys Leu Ile Gly Arg Ala Arg Gly Tyr His Gly Val Asn Val Ala Gly
145                 150                 155                 160 acc agc ctc ggc ggg atc ggt ggc aac cgc aag atg ttc ggc cag ctg    528
Thr Ser Leu Gly Gly Ile Gly Gly Asn Arg Lys Met Phe Gly Gln Leu
                165                 170                 175 atg gac gtc gac cat ctg ccg cac acc ctt caa ccg ggc atg gcg ttc    576
Met Asp Val Asp His Leu Pro His Thr Leu Gln Pro Gly Met Ala Phe
            180                 185                 190 acc cgc ggg atg gcc cag acc ggc ggc gtc gag ctg gcc aac gag ctg    624
Thr Arg Gly Met Ala Gln Thr Gly Gly Val Glu Leu Ala Asn Glu Leu
        195                 200                 205 ctc aag ctg atc gaa ctg cac gac gcc tcg aac atc gcc gcg gtg atc    672
Leu Lys Leu Ile Glu Leu His Asp Ala Ser Asn Ile Ala Ala Val Ile
210                 215                 220 gtc gag ccg atg tcc ggc tcc gcc ggc gta ctg gta ccg ccg gtc ggc    720
Val Glu Pro Met Ser Gly Ser Ala Gly Val Leu Val Pro Pro Val Gly
225                 230                 235                 240 tac ctg cag cgc ctg cgc gag atc tgc gac cag cac aac atc ctg ctg    768
Tyr Leu Gln Arg Leu Arg Glu Ile Cys Asp Gln His Asn Ile Leu Leu
                245                 250                 255 atc ttc gac gag gtg atc acc gcc ttc ggc cgc ctg ggc acc tac agc    816
Ile Phe Asp Glu Val Ile Thr Ala Phe Gly Arg Leu Gly Thr Tyr Ser
            260                 265                 270 ggc gcc gag tac ttc ggc gtc acc ccg gac ctg atg aac gtc gcc aag    864
Gly Ala Glu Tyr Phe Gly Val Thr Pro Asp Leu Met Asn Val Ala Lys
        275                 280                 285 cag gtc acc aac ggc gcc gtg ccg atg ggc gcg gtg atc gcc agc agc    912
Gln Val Thr Asn Gly Ala Val Pro Met Gly Ala Val Ile Ala Ser Ser
    290                 295                 300 gag atc tac gac acc ttc atg aac cag gcg ctg ccc gag cac gcg gtg    960
Glu Ile Tyr Asp Thr Phe Met Asn Gln Ala Leu Pro Glu His Ala Val
305                 310                 315                 320 gag ttc agc cac ggc tac acc tac tcc gcg cac ccg gtc gcc tgc gcc   1008
Glu Phe Ser His Gly Tyr Thr Tyr Ser Ala His Pro Val Ala Cys Ala
                325                 330                 335 gcc ggc ctc gcc gcg ctg gac atc ctg gcc agg gac aac ctg gtg cag   1056
Ala Gly Leu Ala Ala Leu Asp Ile Leu Ala Arg Asp Asn Leu Val Gln
            340                 345                 350 cag tcc gcc gag ctg gcg ccg cac ttc gag aag ggc ctg cac ggc ctg   1104
Gln Ser Ala Glu Leu Ala Pro His Phe Glu Lys Gly Leu His Gly Leu
        355                 360                 365
```

-continued

```
caa ggc gcg aag aac gtc atc gac atc cgc aac tgc ggc ctg gcc ggc      1152
Gln Gly Ala Lys Asn Val Ile Asp Ile Arg Asn Cys Gly Leu Ala Gly
    370             375                 380 gcg atc cag atc gcc ccg cgc gac ggc gat ccg acc gtg cgt ccg ttc      1200
Ala Ile Gln Ile Ala Pro Arg Asp Gly Asp Pro Thr Val Arg Pro Phe
385             390                 395                 400 gag gcc ggc atg aag ctc tgg caa cag ggt ttc tac gtg cgc ttc ggc      1248
Glu Ala Gly Met Lys Leu Trp Gln Gln Gly Phe Tyr Val Arg Phe Gly
                405                 410                 415 ggc gat acc ctg caa ttc ggc ccg acc ttc aac gcc agg ccg gaa gag      1296
Gly Asp Thr Leu Gln Phe Gly Pro Thr Phe Asn Ala Arg Pro Glu Glu
        420                 425                 430 ctg gac cgc ctg ttc gac gcg gtc ggc gaa gcg ctc aac ggc atc gcc      1344
Leu Asp Arg Leu Phe Asp Ala Val Gly Glu Ala Leu Asn Gly Ile Ala
            435                 440                 445 tga                                                                  1347
```

<210> SEQ ID NO 20
<211> LENGTH: 448
<212> TYPE: PRT
<213> ORGANISM: Pseudomonas aeruginosa

<400> SEQUENCE: 20

```
Met Asn Gln Pro Leu Asn Val Ala Pro Pro Val Ser Ser Glu Leu Asn
1               5                   10                  15

Leu Arg Ala His Trp Met Pro Phe Ser Ala Asn Arg Asn Phe Gln Lys
            20                  25                  30

Asp Pro Arg Ile Ile Val Ala Ala Glu Gly Ser Trp Leu Thr Asp Asp
        35                  40                  45

Lys Gly Arg Lys Val Tyr Asp Ser Leu Ser Gly Leu Trp Thr Cys Gly
    50                  55                  60

Ala Gly His Ser Arg Lys Glu Ile Gln Glu Ala Val Ala Arg Gln Leu
65                  70                  75                  80

Gly Thr Leu Asp Tyr Ser Pro Gly Phe Gln Tyr Gly His Pro Leu Ser
                85                  90                  95

Phe Gln Leu Ala Glu Lys Ile Ala Gly Leu Leu Pro Gly Glu Leu Asn
            100                 105                 110

His Val Phe Phe Thr Gly Ser Gly Ser Glu Cys Ala Asp Thr Ser Ile
        115                 120                 125

Lys Met Ala Arg Ala Tyr Trp Arg Leu Lys Gly Gln Pro Gln Lys Thr
    130                 135                 140

Lys Leu Ile Gly Arg Ala Arg Gly Tyr His Gly Val Asn Val Ala Gly
145                 150                 155                 160

Thr Ser Leu Gly Gly Ile Gly Gly Asn Arg Lys Met Phe Gly Gln Leu
                165                 170                 175

Met Asp Val Asp His Leu Pro His Thr Leu Gln Pro Gly Met Ala Phe
            180                 185                 190

Thr Arg Gly Met Ala Gln Thr Gly Gly Val Glu Leu Ala Asn Glu Leu
        195                 200                 205

Leu Lys Leu Ile Glu Leu His Asp Ala Ser Asn Ile Ala Ala Val Ile
    210                 215                 220

Val Glu Pro Met Ser Gly Ser Ala Gly Val Leu Val Pro Pro Val Gly
225                 230                 235                 240

Tyr Leu Gln Arg Leu Arg Glu Ile Cys Asp Gln His Asn Ile Leu Leu
                245                 250                 255
```

```
Ile Phe Asp Glu Val Ile Thr Ala Phe Gly Arg Leu Gly Thr Tyr Ser
            260                 265                 270

Gly Ala Glu Tyr Phe Gly Val Thr Pro Asp Leu Met Asn Val Ala Lys
        275                 280                 285

Gln Val Thr Asn Gly Ala Val Pro Met Gly Ala Val Ile Ala Ser Ser
    290                 295                 300

Glu Ile Tyr Asp Thr Phe Met Asn Gln Ala Leu Pro Glu His Ala Val
305                 310                 315                 320

Glu Phe Ser His Gly Tyr Thr Tyr Ser Ala His Pro Val Ala Cys Ala
                325                 330                 335

Ala Gly Leu Ala Ala Leu Asp Ile Leu Ala Arg Asp Asn Leu Val Gln
            340                 345                 350

Gln Ser Ala Glu Leu Ala Pro His Phe Glu Lys Gly Leu His Gly Leu
        355                 360                 365

Gln Gly Ala Lys Asn Val Ile Asp Ile Arg Asn Cys Gly Leu Ala Gly
    370                 375                 380

Ala Ile Gln Ile Ala Pro Arg Asp Gly Asp Pro Thr Val Arg Pro Phe
385                 390                 395                 400

Glu Ala Gly Met Lys Leu Trp Gln Gln Gly Phe Tyr Val Arg Phe Gly
                405                 410                 415

Gly Asp Thr Leu Gln Phe Gly Pro Thr Phe Asn Ala Arg Pro Glu Glu
            420                 425                 430

Leu Asp Arg Leu Phe Asp Ala Val Gly Glu Ala Leu Asn Gly Ile Ala
        435                 440                 445

<210> SEQ ID NO 21
<211> LENGTH: 1416
<212> TYPE: DNA
<213> ORGANISM: Bacillus subtilis
<220> FEATURE:
<221> NAME/KEY: CDS
<222> LOCATION: (1)..(1413)

<400> SEQUENCE: 21 atg aaa aac aaa tgg tat aaa ccg aaa cgg cat tgg aag gag atc gag    48
Met Lys Asn Lys Trp Tyr Lys Pro Lys Arg His Trp Lys Glu Ile Glu
1               5                   10                  15 tta tgg aag gac gtt ccg gaa gag aaa tgg aac gat tgg ctt tgg cag    96
Leu Trp Lys Asp Val Pro Glu Glu Lys Trp Asn Asp Trp Leu Trp Gln
            20                  25                  30 ctg aca cac act gta aga acg tta gat gat tta aag aaa gtc att aat   144
Leu Thr His Thr Val Arg Thr Leu Asp Asp Leu Lys Lys Val Ile Asn
        35                  40                  45 ctg acc gag gat gaa gag gaa ggc gtc cgt att tct acc aaa acg atc   192
Leu Thr Glu Asp Glu Glu Glu Gly Val Arg Ile Ser Thr Lys Thr Ile
    50                  55                  60 ccc tta aat att aca cct tac tat gct tct tta atg gac ccc gac aat   240
Pro Leu Asn Ile Thr Pro Tyr Tyr Ala Ser Leu Met Asp Pro Asp Asn
65                  70                  75                  80 ccg aga tgc ccg gta cgc atg cag tct gtg ccg ctt tct gaa gaa atg   288
Pro Arg Cys Pro Val Arg Met Gln Ser Val Pro Leu Ser Glu Glu Met
                85                  90                  95 cac aaa aca aaa tac gat atg gaa gac ccg ctt cat gag gat gaa gat   336
His Lys Thr Lys Tyr Asp Met Glu Asp Pro Leu His Glu Asp Glu Asp
            100                 105                 110 tca ccg gta ccc ggt ctg aca cac cgc tat ccc gac cgt gtg ctg ttt   384
Ser Pro Val Pro Gly Leu Thr His Arg Tyr Pro Asp Arg Val Leu Phe
        115                 120                 125
```

```
ctt gtc acg aat caa tgt tcc gtg tac tgc cgc cac tgc aca cgc cgg    432
Leu Val Thr Asn Gln Cys Ser Val Tyr Cys Arg His Cys Thr Arg Arg
    130                 135                 140 cgc ttt tcc gga caa atc gga atg ggc gtc ccc aaa aaa cag ctt gat    480
Arg Phe Ser Gly Gln Ile Gly Met Gly Val Pro Lys Lys Gln Leu Asp
145                 150                 155                 160 gct gca att gct tat atc cgg gaa aca ccc gaa atc cgc gat tgt tta    528
Ala Ala Ile Ala Tyr Ile Arg Glu Thr Pro Glu Ile Arg Asp Cys Leu
                165                 170                 175 att tca ggc ggt gat ggg ctg ctc atc aac gac caa att tta gaa tat    576
Ile Ser Gly Gly Asp Gly Leu Leu Ile Asn Asp Gln Ile Leu Glu Tyr
            180                 185                 190 att tta aaa gag ctg cgc agc att ccg cat ctg gaa gtc atc cgc atc    624
Ile Leu Lys Glu Leu Arg Ser Ile Pro His Leu Glu Val Ile Arg Ile
        195                 200                 205 gga aca cgt gct ccc gtc gtc ttt ccg cag cgc att acc gat cat ctg    672
Gly Thr Arg Ala Pro Val Val Phe Pro Gln Arg Ile Thr Asp His Leu
    210                 215                 220 tgc gag ata ttg aaa aaa tat cat ccg gtc tgg ctg aac acc cat ttt    720
Cys Glu Ile Leu Lys Lys Tyr His Pro Val Trp Leu Asn Thr His Phe
225                 230                 235                 240 aac aca agc atc gaa atg aca gaa gaa tcc gtt gag gca tgt gaa aag    768
Asn Thr Ser Ile Glu Met Thr Glu Glu Ser Val Glu Ala Cys Glu Lys
                245                 250                 255 ctg gtg aac gcg gga gtg ccg gtc gga aat cag gct gtc gta tta gca    816
Leu Val Asn Ala Gly Val Pro Val Gly Asn Gln Ala Val Val Leu Ala
            260                 265                 270 ggt att aat gat tcg gtt cca att atg aaa aag ctc atg cat gac ttg    864
Gly Ile Asn Asp Ser Val Pro Ile Met Lys Lys Leu Met His Asp Leu
        275                 280                 285 gta aaa atc aga gtc cgt cct tat tat att tac caa tgt gat ctg tca    912
Val Lys Ile Arg Val Arg Pro Tyr Tyr Ile Tyr Gln Cys Asp Leu Ser
    290                 295                 300 gaa gga ata ggg cat ttc cgt gct cct gtt tcc aaa ggt ttg gag atc    960
Glu Gly Ile Gly His Phe Arg Ala Pro Val Ser Lys Gly Leu Glu Ile
305                 310                 315                 320 att gaa ggg ctg aga ggt cat acc tca ggc tat gcg gtt cct acc ttt   1008
Ile Glu Gly Leu Arg Gly His Thr Ser Gly Tyr Ala Val Pro Thr Phe
                325                 330                 335 gtc gtt cac gca cca ggc gga gga ggt aaa atc gcc ctg cag ccg aac   1056
Val Val His Ala Pro Gly Gly Gly Gly Lys Ile Ala Leu Gln Pro Asn
            340                 345                 350 tat gtc ctg tca caa agt cct gac aaa gtg atc tta aga aat ttt gaa   1104
Tyr Val Leu Ser Gln Ser Pro Asp Lys Val Ile Leu Arg Asn Phe Glu
        355                 360                 365 ggt gtg att acg tca tat ccg gaa cca gag aat tat atc ccc aat cag   1152
Gly Val Ile Thr Ser Tyr Pro Glu Pro Glu Asn Tyr Ile Pro Asn Gln
    370                 375                 380 gca gac gcc tat ttt gag tcc gtt ttc cct gaa acc gct gac aaa aag   1200
Ala Asp Ala Tyr Phe Glu Ser Val Phe Pro Glu Thr Ala Asp Lys Lys
385                 390                 395                 400 gag ccg atc ggg ctg agt gcc att ttt gct gac aaa gaa gtt tcg ttt   1248
Glu Pro Ile Gly Leu Ser Ala Ile Phe Ala Asp Lys Glu Val Ser Phe
                405                 410                 415 aca cct gaa aat gta gac aga atc aaa cgg cgt gag gca tac atc gca   1296
Thr Pro Glu Asn Val Asp Arg Ile Lys Arg Arg Glu Ala Tyr Ile Ala
            420                 425                 430 aat ccg gag cat gaa aca tta aaa gat cgg cgt gag aaa aga gat cag   1344
Asn Pro Glu His Glu Thr Leu Lys Asp Arg Arg Glu Lys Arg Asp Gln
        435                 440                 445
```

```
ctc aaa gaa aag aaa ttt ttg gcg cag cag aaa aaa cag aaa gag act    1392
Leu Lys Glu Lys Lys Phe Leu Ala Gln Gln Lys Lys Gln Lys Glu Thr
450                 455                 460 gaa tgc gga ggg gat tct tca tga                                    1416
Glu Cys Gly Gly Asp Ser Ser
465                 470

<210> SEQ ID NO 22
<211> LENGTH: 471
<212> TYPE: PRT
<213> ORGANISM: Bacillus subtilis

<400> SEQUENCE: 22

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Gly Val Arg Ile Ser Thr Lys Thr Ile
50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg His Cys Thr Arg Arg
130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335
```

```
Val Val His Ala Pro Gly Gly Gly Lys Ile Ala Leu Gln Pro Asn
            340                 345                 350

Tyr Val Leu Ser Gln Ser Pro Asp Lys Val Ile Leu Arg Asn Phe Glu
            355                 360                 365

Gly Val Ile Thr Ser Tyr Pro Glu Pro Glu Asn Tyr Ile Pro Asn Gln
            370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
            435                 440                 445

Leu Lys Glu Lys Lys Phe Leu Ala Gln Gln Lys Lys Gln Lys Glu Thr
            450                 455                 460

Glu Cys Gly Gly Asp Ser Ser
465                 470
```

<210> SEQ ID NO 23
<211> LENGTH: 1416
<212> TYPE: DNA
<213> ORGANISM: Bacillus subtilis
<220> FEATURE:
<221> NAME/KEY: CDS
<222> LOCATION: (1)..(1413)

<400> SEQUENCE: 23

```
atg aaa aac aaa tgg tat aaa ccg aaa cgg cat tgg aag gag atc gag     48
Met Lys Asn Lys Trp Tyr Lys Pro Lys Arg His Trp Lys Glu Ile Glu
1               5                   10                  15 tta tgg aag gac gtt ccg gaa gag aaa tgg aac gat tgg ctt tgg cag     96
Leu Trp Lys Asp Val Pro Glu Glu Lys Trp Asn Asp Trp Leu Trp Gln
            20                  25                  30 ctg aca cac act gta aga acg tta gat gat tta aag aaa gtc att aat    144
Leu Thr His Thr Val Arg Thr Leu Asp Asp Leu Lys Lys Val Ile Asn
        35                  40                  45 ctg acc gag gat gaa gag gaa ggc gtc aga att tct acc aaa acg atc    192
Leu Thr Glu Asp Glu Glu Glu Gly Val Arg Ile Ser Thr Lys Thr Ile
    50                  55                  60 ccc tta aat att aca cct tac tat gct tct tta atg gac ccc gac aat    240
Pro Leu Asn Ile Thr Pro Tyr Tyr Ala Ser Leu Met Asp Pro Asp Asn
65                  70                  75                  80 ccg aga tgc ccg gta cgc atg cag tct gtg ccg ctt tct gaa gaa atg    288
Pro Arg Cys Pro Val Arg Met Gln Ser Val Pro Leu Ser Glu Glu Met
                85                  90                  95 cac aaa aca aaa tac gat atg gaa gac ccg ctt cat gag gat gaa gat    336
His Lys Thr Lys Tyr Asp Met Glu Asp Pro Leu His Glu Asp Glu Asp
            100                 105                 110 tca ccg gta ccc ggt ctg aca cac cgc tat ccc gac cgt gtg ctg ttt    384
Ser Pro Val Pro Gly Leu Thr His Arg Tyr Pro Asp Arg Val Leu Phe
        115                 120                 125 ctt gtc acg aat caa tgt tcc gtg tac tgc cgc tac tgc aca aga agg    432
Leu Val Thr Asn Gln Cys Ser Val Tyr Cys Arg Tyr Cys Thr Arg Arg
    130                 135                 140 cgc ttt tcc gga caa atc gga atg ggt gtc ccc aaa aaa cag ctt gat    480
Arg Phe Ser Gly Gln Ile Gly Met Gly Val Pro Lys Lys Gln Leu Asp
145                 150                 155                 160
```

```
gct gca att gct tat atc cgg gaa aca ccc gaa atc cgc gat tgt tta     528
Ala Ala Ile Ala Tyr Ile Arg Glu Thr Pro Glu Ile Arg Asp Cys Leu
            165                 170                 175 att tca ggc ggt gat ggg ctg ctc atc aac gac caa att tta gaa tat     576
Ile Ser Gly Gly Asp Gly Leu Leu Ile Asn Asp Gln Ile Leu Glu Tyr
        180                 185                 190 att tta aaa gag ctg cgc agc att ccg cat ctg gaa gtc atc aga atc     624
Ile Leu Lys Glu Leu Arg Ser Ile Pro His Leu Glu Val Ile Arg Ile
    195                 200                 205 gga aca aga gct ccc gtc gtc ttt ccg cag cgc att acc gat cat ctg     672
Gly Thr Arg Ala Pro Val Val Phe Pro Gln Arg Ile Thr Asp His Leu
210                 215                 220 tgc gag ata ttg aaa aaa tat cat ccg gtc tgg ctg aac acc cat ttt     720
Cys Glu Ile Leu Lys Lys Tyr His Pro Val Trp Leu Asn Thr His Phe
225                 230                 235                 240 aac aca agc atc gaa atg aca gaa gaa tcc gtt gag gca tgt gaa aag     768
Asn Thr Ser Ile Glu Met Thr Glu Glu Ser Val Glu Ala Cys Glu Lys
            245                 250                 255 ctg gtg aac gcg gga gtg ccg gtc gga aat cag gct gtc gta tta gca     816
Leu Val Asn Ala Gly Val Pro Val Gly Asn Gln Ala Val Val Leu Ala
        260                 265                 270 ggt att aat gat tcg gtt cca att atg aaa aag ctc atg cat gac ttg     864
Gly Ile Asn Asp Ser Val Pro Ile Met Lys Lys Leu Met His Asp Leu
    275                 280                 285 gta aaa atc aga gtc cgt cct tat tat att tac caa tgt gat ctg tca     912
Val Lys Ile Arg Val Arg Pro Tyr Tyr Ile Tyr Gln Cys Asp Leu Ser
290                 295                 300 gaa gga ata ggg cat ttc aga gct cct gtt tcc aaa ggt ttg gag atc     960
Glu Gly Ile Gly His Phe Arg Ala Pro Val Ser Lys Gly Leu Glu Ile
305                 310                 315                 320 att gaa ggg ctg aga ggt cat acc tca ggc tat gcg gtt cct acc ttt    1008
Ile Glu Gly Leu Arg Gly His Thr Ser Gly Tyr Ala Val Pro Thr Phe
            325                 330                 335 gtc gtt cac gca cca ggc gga gga ggt aaa atc gcc ctg cag ccg aac    1056
Val Val His Ala Pro Gly Gly Gly Gly Lys Ile Ala Leu Gln Pro Asn
        340                 345                 350 tat gtc ctg tca caa agt cct gac aaa gtg atc tta aga aat ttt gaa    1104
Tyr Val Leu Ser Gln Ser Pro Asp Lys Val Ile Leu Arg Asn Phe Glu
    355                 360                 365 ggt gtg att acg tca tat ccg gaa cca gag aat tat atc ccc aat cag    1152
Gly Val Ile Thr Ser Tyr Pro Glu Pro Glu Asn Tyr Ile Pro Asn Gln
370                 375                 380 gca gac gcc tat ttt gag tcc gtt ttc cct gaa acc gct gac aaa aag    1200
Ala Asp Ala Tyr Phe Glu Ser Val Phe Pro Glu Thr Ala Asp Lys Lys
385                 390                 395                 400 gag ccg atc ggg ctg agt gcc att ttt gct gac aaa gaa gtt tcg ttt    1248
Glu Pro Ile Gly Leu Ser Ala Ile Phe Ala Asp Lys Glu Val Ser Phe
            405                 410                 415 aca cct gaa aat gta gac aga atc aaa agg aga gag gca tac atc gca    1296
Thr Pro Glu Asn Val Asp Arg Ile Lys Arg Arg Glu Ala Tyr Ile Ala
        420                 425                 430 aat ccg gag cat gaa aca tta aaa gat cgg cgt gag aaa aga gat cag    1344
Asn Pro Glu His Glu Thr Leu Lys Asp Arg Arg Glu Lys Arg Asp Gln
    435                 440                 445 ctc aaa gaa aag aaa ttt ttg gcg cag cag aaa aaa cag aaa gag act    1392
Leu Lys Glu Lys Lys Phe Leu Ala Gln Gln Lys Lys Gln Lys Glu Thr
450                 455                 460 gaa tgc gga ggg gat tct tca tga                                    1416
Glu Cys Gly Gly Asp Ser Ser
465                 470
```

```
<210> SEQ ID NO 24
<211> LENGTH: 471
<212> TYPE: PRT
<213> ORGANISM: Bacillus subtilis

<400> SEQUENCE: 24

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Gly Val Arg Ile Ser Thr Lys Thr Ile
 50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380
```

```
Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
            405                 410                 415

Thr Pro Glu Asn Val Asp Arg Ile Lys Arg Arg Glu Ala Tyr Ile Ala
        420                 425                 430

Asn Pro Glu His Glu Thr Leu Lys Asp Arg Arg Glu Lys Arg Asp Gln
            435                 440                 445

Leu Lys Glu Lys Lys Phe Leu Ala Gln Gln Lys Lys Gln Lys Glu Thr
        450                 455                 460

Glu Cys Gly Gly Asp Ser Ser
465                 470

<210> SEQ ID NO 25
<211> LENGTH: 1251
<212> TYPE: DNA
<213> ORGANISM: Porphyromonas gingivalis
<220> FEATURE:
<221> NAME/KEY: CDS
<222> LOCATION: (1)..(1248)

<400> SEQUENCE: 25
```

| | | | | | | | | | | | | | | | | |
|---|---|---|---|---|---|---|---|---|---|---|---|---|---|---|---|---|
| atg | gca | gaa | agt | cgt | aga | aag | tat | tat | ttc | cct | gat | gtc | acc | gat | gag | 48 |
| Met | Ala | Glu | Ser | Arg | Arg | Lys | Tyr | Tyr | Phe | Pro | Asp | Val | Thr | Asp | Glu | |
| 1 | | | 5 | | | | | 10 | | | | | 15 | | | |
| caa | tgg | tac | gac | tgg | cat | tgg | cag | gtc | ctc | aat | cga | att | gag | acg | ctc | 96 |
| Gln | Trp | Tyr | Asp | Trp | His | Trp | Gln | Val | Leu | Asn | Arg | Ile | Glu | Thr | Leu | |
| | | | 20 | | | | | 25 | | | | | 30 | | | |
| gac | cag | ctg | aaa | aag | tac | gtt | aca | ctc | acc | gct | gaa | gaa | gaa | gag | gga | 144 |
| Asp | Gln | Leu | Lys | Lys | Tyr | Val | Thr | Leu | Thr | Ala | Glu | Glu | Glu | Glu | Gly | |
| | | | 35 | | | | | 40 | | | | | 45 | | | |
| gta | aaa | gaa | tcg | ccc | aaa | gta | ctc | cga | atg | gct | atc | aca | cct | tat | tat | 192 |
| Val | Lys | Glu | Ser | Pro | Lys | Val | Leu | Arg | Met | Ala | Ile | Thr | Pro | Tyr | Tyr | |
| | 50 | | | | | 55 | | | | | 60 | | | | | |
| ttg | agt | ttg | ata | gac | ccc | gag | aat | cct | aat | tgt | ccg | att | cgt | aaa | caa | 240 |
| Leu | Ser | Leu | Ile | Asp | Pro | Glu | Asn | Pro | Asn | Cys | Pro | Ile | Arg | Lys | Gln | |
| 65 | | | | | 70 | | | | | 75 | | | | | 80 | |
| gcc | att | cct | act | caa | cag | gaa | ctg | gta | cgt | gct | cct | gaa | gat | cag | gta | 288 |
| Ala | Ile | Pro | Thr | Gln | Gln | Glu | Leu | Val | Arg | Ala | Pro | Glu | Asp | Gln | Val | |
| | | | | 85 | | | | | 90 | | | | | 95 | | |
| gac | cca | ctt | agt | gaa | gat | gaa | gat | tcg | ccc | gta | ccc | gga | ctg | act | cat | 336 |
| Asp | Pro | Leu | Ser | Glu | Asp | Glu | Asp | Ser | Pro | Val | Pro | Gly | Leu | Thr | His | |
| | | | | 100 | | | | | 105 | | | | | 110 | | |
| cgt | tat | ccg | gat | cgt | gta | ttg | ttc | ctt | atc | acg | gac | aaa | tgt | tcg | atg | 384 |
| Arg | Tyr | Pro | Asp | Arg | Val | Leu | Phe | Leu | Ile | Thr | Asp | Lys | Cys | Ser | Met | |
| | | | 115 | | | | | 120 | | | | | 125 | | | |
| tac | tgt | cgt | cat | tgt | act | cgc | cgt | cgc | ttc | gca | gga | cag | aaa | gat | gct | 432 |
| Tyr | Cys | Arg | His | Cys | Thr | Arg | Arg | Arg | Phe | Ala | Gly | Gln | Lys | Asp | Ala | |
| | | | 130 | | | | | 135 | | | | | 140 | | | |
| tct | tct | cct | tct | gag | cgc | atc | gat | cga | tgc | att | gac | tat | ata | gcc | aat | 480 |
| Ser | Ser | Pro | Ser | Glu | Arg | Ile | Asp | Arg | Cys | Ile | Asp | Tyr | Ile | Ala | Asn | |
| 145 | | | | | 150 | | | | | 155 | | | | | 160 | |
| aca | ccg | aca | gtc | cgc | gat | gtt | ttg | cta | tcg | gga | ggc | gat | gcc | ctc | ctt | 528 |
| Thr | Pro | Thr | Val | Arg | Asp | Val | Leu | Leu | Ser | Gly | Gly | Asp | Ala | Leu | Leu | |
| | | | | 165 | | | | | 170 | | | | | 175 | | |
| gtc | agc | gac | gaa | cgc | ttg | gaa | tac | ata | ttg | aag | cgt | ctg | cgc | gaa | ata | 576 |
| Val | Ser | Asp | Glu | Arg | Leu | Glu | Tyr | Ile | Leu | Lys | Arg | Leu | Arg | Glu | Ile | |
| | | | | 180 | | | | | 185 | | | | | 190 | | |

```
                                      -continued
cct cat gtg gag att gtt cgt ata gga agc cgt acg ccg gta gtc ctc      624
Pro His Val Glu Ile Val Arg Ile Gly Ser Arg Thr Pro Val Val Leu
        195                 200                 205 cct cag cgt ata acg cct caa ttg gtg gat atg ctc aaa aaa tat cat      672
Pro Gln Arg Ile Thr Pro Gln Leu Val Asp Met Leu Lys Lys Tyr His
    210                 215                 220 ccg gtg tgg ctg aac act cac ttc aac cac ccg aat gaa gtt acc gaa      720
Pro Val Trp Leu Asn Thr His Phe Asn His Pro Asn Glu Val Thr Glu
225                 230                 235                 240 gaa gca gta gag gct tgt gaa aga atg gcc aat gcc ggt att ccg ttg      768
Glu Ala Val Glu Ala Cys Glu Arg Met Ala Asn Ala Gly Ile Pro Leu
            245                 250                 255 ggt aac caa acg gtt tta ttg cgt gga atc aat gat tgt aca cat gtg      816
Gly Asn Gln Thr Val Leu Leu Arg Gly Ile Asn Asp Cys Thr His Val
        260                 265                 270 atg aag aga ttg gta cat ttg ctg gta aag atg cgt gtg cgt cct tac      864
Met Lys Arg Leu Val His Leu Leu Val Lys Met Arg Val Arg Pro Tyr
    275                 280                 285 tat ata tat gta tgc gat ctt tcg ctt gga ata ggt cat ttc cgc acg      912
Tyr Ile Tyr Val Cys Asp Leu Ser Leu Gly Ile Gly His Phe Arg Thr
290                 295                 300 ccg gta tct aaa gga atc gaa att atc gaa aat ttg cgc gga cac acc      960
Pro Val Ser Lys Gly Ile Glu Ile Ile Glu Asn Leu Arg Gly His Thr
305                 310                 315                 320 tcg ggc tat gca gtt cct acc ttt gtg gta ggt gct ccg ggg ggt ggt     1008
Ser Gly Tyr Ala Val Pro Thr Phe Val Val Gly Ala Pro Gly Gly Gly
            325                 330                 335 ggt aag ata cct gta acg ccg aac tat gtt gta tct cag tcc cca cga     1056
Gly Lys Ile Pro Val Thr Pro Asn Tyr Val Val Ser Gln Ser Pro Arg
        340                 345                 350 cat gtg gtt ctt cgc aat tat gaa ggt gtt atc aca acc tat acg gag     1104
His Val Val Leu Arg Asn Tyr Glu Gly Val Ile Thr Thr Tyr Thr Glu
    355                 360                 365 ccg gag aat tat cat gag gag tgc gat tgt gag gac tgt cga gcc ggt     1152
Pro Glu Asn Tyr His Glu Glu Cys Asp Cys Glu Asp Cys Arg Ala Gly
370                 375                 380 aag cat aaa gag ggt gta gct gca ctt tcc gga ggt cag cag ttg gct     1200
Lys His Lys Glu Gly Val Ala Ala Leu Ser Gly Gly Gln Gln Leu Ala
385                 390                 395                 400 atc gag cct tcc gac tta gct cgc aaa aaa cgc aag ttt gat aag aac     1248
Ile Glu Pro Ser Asp Leu Ala Arg Lys Lys Arg Lys Phe Asp Lys Asn
            405                 410                 415 tga                                                                 1251

<210> SEQ ID NO 26
<211> LENGTH: 416
<212> TYPE: PRT
<213> ORGANISM: Porphyromonas gingivalis

<400> SEQUENCE: 26

Met Ala Glu Ser Arg Arg Lys Tyr Tyr Phe Pro Asp Val Thr Asp Glu
1               5                   10                  15

Gln Trp Tyr Asp Trp His Trp Gln Val Leu Asn Arg Ile Glu Thr Leu
            20                  25                  30

Asp Gln Leu Lys Lys Tyr Val Thr Leu Thr Ala Glu Glu Glu Glu Gly
        35                  40                  45

Val Lys Glu Ser Pro Lys Val Leu Arg Met Ala Ile Thr Pro Tyr Tyr
    50                  55                  60
```

```
Leu Ser Leu Ile Asp Pro Glu Asn Pro Asn Cys Pro Ile Arg Lys Gln
 65                  70                  75                  80

Ala Ile Pro Thr Gln Gln Glu Leu Val Arg Ala Pro Glu Asp Gln Val
             85                  90                  95

Asp Pro Leu Ser Glu Asp Glu Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Phe Ala Gly Gln Lys Asp Ala
    130                 135                 140

Ser Ser Pro Ser Glu Arg Ile Asp Arg Cys Ile Asp Tyr Ile Ala Asn
145                 150                 155                 160

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Ile
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
225                 230                 235                 240

Glu Ala Val Glu Ala Cys Glu Arg Met Ala Asn Ala Gly Ile Pro Leu
                245                 250                 255

Gly Asn Gln Thr Val Leu Leu Arg Gly Ile Asn Asp Cys Thr His Val
            260                 265                 270

Met Lys Arg Leu Val His Leu Leu Val Lys Met Arg Val Arg Pro Tyr
        275                 280                 285

Tyr Ile Tyr Val Cys Asp Leu Ser Leu Gly Ile Gly His Phe Arg Thr
    290                 295                 300

Pro Val Ser Lys Gly Ile Glu Ile Ile Glu Asn Leu Arg Gly His Thr
305                 310                 315                 320

Ser Gly Tyr Ala Val Pro Thr Phe Val Val Gly Ala Pro Gly Gly Gly
                325                 330                 335

Gly Lys Ile Pro Val Thr Pro Asn Tyr Val Ser Gln Ser Pro Arg
            340                 345                 350

His Val Val Leu Arg Asn Tyr Glu Gly Val Ile Thr Thr Tyr Thr Glu
        355                 360                 365

Pro Glu Asn Tyr His Glu Glu Cys Asp Cys Glu Asp Cys Arg Ala Gly
    370                 375                 380

Lys His Lys Glu Gly Val Ala Ala Leu Ser Gly Gly Gln Gln Leu Ala
385                 390                 395                 400

Ile Glu Pro Ser Asp Leu Ala Arg Lys Lys Arg Lys Phe Asp Lys Asn
                405                 410                 415

<210> SEQ ID NO 27
<211> LENGTH: 897
<212> TYPE: DNA
<213> ORGANISM: Pseudomonas aeruginosa
<220> FEATURE:
<221> NAME/KEY: CDS
<222> LOCATION: (1)..(894)
```

<400> SEQUENCE: 27

```
atg acc gac atc gca ttc ctc ggc ctg ggc aac atg ggt ggg ccg atg      48
Met Thr Asp Ile Ala Phe Leu Gly Leu Gly Asn Met Gly Gly Pro Met
 1               5                  10                  15 gcc gcc aac ctg ctc aag gcc ggc cac cgg gtg aat gtc ttc gac ttg      96
Ala Ala Asn Leu Leu Lys Ala Gly His Arg Val Asn Val Phe Asp Leu
                20                  25                  30 cag ccc aag gcc gtg ctg ggc ctg gtc gag cag ggc gcg cag ggc gcc     144
Gln Pro Lys Ala Val Leu Gly Leu Val Glu Gln Gly Ala Gln Gly Ala
            35                  40                  45 gat agc gcc ttg cag tgc tgc gaa ggc gcc gaa gtg gtg atc agc atg     192
Asp Ser Ala Leu Gln Cys Cys Glu Gly Ala Glu Val Val Ile Ser Met
        50                  55                  60 ctg ccg gcc ggg cag cac gtg gaa agc ctg tat ctc ggc gac gac ggc     240
Leu Pro Ala Gly Gln His Val Glu Ser Leu Tyr Leu Gly Asp Asp Gly
 65                  70                  75                  80 ctg ctc gcg cgg gtc gcc ggc aag ccc ctg ctg atc gac tgc tcg acc     288
Leu Leu Ala Arg Val Ala Gly Lys Pro Leu Leu Ile Asp Cys Ser Thr
                 85                  90                  95 atc gcc ccg gag acc gcg cgc aag gtc gcc gag gcc gcc gcg gcg aag     336
Ile Ala Pro Glu Thr Ala Arg Lys Val Ala Glu Ala Ala Ala Ala Lys
            100                 105                 110 ggc ctg acc ctg ctc gac gcg ccg gtt tcc ggc ggc gtc ggc ggc gcc     384
Gly Leu Thr Leu Leu Asp Ala Pro Val Ser Gly Gly Val Gly Gly Ala
        115                 120                 125 cgc gcc ggc acc ctg agc ttc atc gtc ggc ggc ccc gcc gaa ggc ttc     432
Arg Ala Gly Thr Leu Ser Phe Ile Val Gly Gly Pro Ala Glu Gly Phe
130                 135                 140 gcg cgg gcc cgg ccg gtc ctc gag aac atg ggc cgg aac atc ttc cac     480
Ala Arg Ala Arg Pro Val Leu Glu Asn Met Gly Arg Asn Ile Phe His
145                 150                 155                 160 gcc ggc gat cac ggc gcc ggc cag gtg gcg aag atc tgc aac aac atg     528
Ala Gly Asp His Gly Ala Gly Gln Val Ala Lys Ile Cys Asn Asn Met
                165                 170                 175 ctc ctc ggc atc ctc atg gcc ggc acc gcc gag gcc ctg gcg ctg ggg     576
Leu Leu Gly Ile Leu Met Ala Gly Thr Ala Glu Ala Leu Ala Leu Gly
            180                 185                 190 gtg aag aac ggc ctc gac ccg gcg gtg ctg tcc gag gtg atg aag cag     624
Val Lys Asn Gly Leu Asp Pro Ala Val Leu Ser Glu Val Met Lys Gln
        195                 200                 205 agt tcc ggc ggc aac tgg gcg ctg aac ctc tac aac ccc tgg ccc ggg     672
Ser Ser Gly Gly Asn Trp Ala Leu Asn Leu Tyr Asn Pro Trp Pro Gly
    210                 215                 220 gtg atg ccg cag gcg ccg gcg agc aac ggc tat gcc ggc ggt ttc cag     720
Val Met Pro Gln Ala Pro Ala Ser Asn Gly Tyr Ala Gly Gly Phe Gln
225                 230                 235                 240 gtg cgc ctg atg aac aag gac ctc ggc ctg gcg ctg gcc aac gcc cag     768
Val Arg Leu Met Asn Lys Asp Leu Gly Leu Ala Leu Ala Asn Ala Gln
                245                 250                 255 gcg gtg cag gcc tcg acg ccg ctc ggc gcg ctg gcg cgc aac ctg ttc     816
Ala Val Gln Ala Ser Thr Pro Leu Gly Ala Leu Ala Arg Asn Leu Phe
            260                 265                 270 agc ctg cac gcc cag gcc gat gcc gag cac gag ggg ctg gac ttc tcc     864
Ser Leu His Ala Gln Ala Asp Ala Glu His Glu Gly Leu Asp Phe Ser
        275                 280                 285 agc atc cag aag ctc tac cgc ggc aag gac taa                         897
Ser Ile Gln Lys Leu Tyr Arg Gly Lys Asp
    290                 295
```

-continued

```
<210> SEQ ID NO 28
<211> LENGTH: 298
<212> TYPE: PRT
<213> ORGANISM: Pseudomonas aeruginosa

<400> SEQUENCE: 28

Met Thr Asp Ile Ala Phe Leu Gly Leu Gly Asn Met Gly Gly Pro Met
1               5                   10                  15

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
65                  70                  75                  80

Leu Leu Ala Arg Val Ala Gly Lys Pro Leu Leu Ile Asp Cys Ser Thr
                85                  90                  95

Ile Ala Pro Glu Thr Ala Arg Lys Val Ala Glu Ala Ala Ala Ala Lys
            100                 105                 110

Gly Leu Thr Leu Leu Asp Ala Pro Val Ser Gly Gly Val Gly Gly Ala
        115                 120                 125

Arg Ala Gly Thr Leu Ser Phe Ile Val Gly Gly Pro Ala Glu Gly Phe
    130                 135                 140

Ala Arg Ala Arg Pro Val Leu Glu Asn Met Gly Arg Asn Ile Phe His
145                 150                 155                 160

Ala Gly Asp His Gly Ala Gly Gln Val Ala Lys Ile Cys Asn Asn Met
                165                 170                 175

Leu Leu Gly Ile Leu Met Ala Gly Thr Ala Glu Ala Leu Ala Leu Gly
            180                 185                 190

Val Lys Asn Gly Leu Asp Pro Ala Val Leu Ser Glu Val Met Lys Gln
        195                 200                 205

Ser Ser Gly Gly Asn Trp Ala Leu Asn Leu Tyr Asn Pro Trp Pro Gly
    210                 215                 220

Val Met Pro Gln Ala Pro Ala Ser Asn Gly Tyr Ala Gly Gly Phe Gln
225                 230                 235                 240

Val Arg Leu Met Asn Lys Asp Leu Gly Leu Ala Leu Ala Asn Ala Gln
                245                 250                 255

Ala Val Gln Ala Ser Thr Pro Leu Gly Ala Leu Ala Arg Asn Leu Phe
            260                 265                 270

Ser Leu His Ala Gln Ala Asp Ala Glu His Glu Gly Leu Asp Phe Ser
        275                 280                 285

Ser Ile Gln Lys Leu Tyr Arg Gly Lys Asp
    290                 295
```

PRODUCTION OF 3-HYDROXYPROPIONIC ACID USING BETA-ALANINE/PYRUVATE AMINOTRANSFERASE

CROSS REFERENCE TO RELATED APPLICATION

This is the U.S. National Stage of International Application No. PCT/US2004/040827, filed Dec. 6, 2004 (published in English under PCT Article 21(2)), which claims the benefit of U.S. Provisional Application No. 60/527,357, filed Dec. 4, 2003, herein incorporated by reference in its entirety.

FIELD

This disclosure relates to cells having beta-alanine/pyruvate aminotransferase activity that can be used to convert beta-alanine to 3-hydroxypropionic acid (3-HP) and other organic compounds.

BACKGROUND

Organic chemicals such as organic acids, esters, and polyols can be used to synthesize plastic materials and other products. To meet the increasing demand for organic chemicals, more efficient and cost-effective production methods are being developed which utilize raw materials based on carbohydrates rather than hydrocarbons. For example, certain bacteria have been used to produce large quantities of lactic acid used in the production of polylactic acid.

3-hydroxypropionic acid (3-HP) is an organic acid. Several chemical synthesis routes have been described to produce 3-HP, and biocatalytic routes have also been disclosed (WO 01/16346 to Suthers et al.). 3-HP has utility for specialty synthesis and can be converted to commercially important intermediates by known art in the chemical industry, such as acrylic acid by dehydration, malonic acid by oxidation, esters by esterification reactions with alcohols, and 1,3-propanediol by reduction.

SUMMARY

The compound 3-hydroxypropionic acid (3-HP) can be produced by biocatalysis from beta-alanine (FIG. 1). Beta-alanine can be synthesized in cells from carnosine, beta-alanyl arginine, beta-alanyl lysine, uracil via 5,6-dihydrouracil and N-carbamoyl-beta-alanine, N-acetyl-beta-alanine, anserine, or aspartate. However, these routes are relatively inefficient because they require rare precursors or starting compounds that are more valuable than 3-HP. As an alternative, beta-alanine can be produced from alpha-alanine by an enzyme having alanine 2,3-aminomutase activity (FIG. 1), such as SEQ ID NOS: 22, 24, and 26, as well as variants, fragments, and fusions thereof that retain alanine 2,3-aminomutase activity. A novel alanine 2,3-aminomutase nucleic acid sequence (SEQ ID NO: 21) and corresponding amino acid sequence (SEQ ID NO: 22), as well as variants, fragments, fusions, and polymorphisms thereof that retain alanine 2,3-aminomutase activity, is disclosed.

Also disclosed are methods of producing 3-HP from beta-alanine using beta-alanine/pyruvate aminotransferase (BAPAT) sequences. In one example, a BAPAT peptide is a sequence that includes SEQ ID NO: 18 or 20, or variants, fragments, or fusions thereof that retain BAPAT activity. Exemplary BAPAT nucleic acid sequences include, but are not limited to, SEQ ID NO: 17 or 19. BAPAT sequences can be used to transform cells, such that the transformed cells have BAPAT activity, which allows the cells to produce 3-HP from beta-alanine through a malonate semialdehyde (3-oxo-propanoate) intermediate.

Transformed cells having BAPAT activity, which allows the cell to convert beta-alanine to 3-HP through a malonate semialdehyde intermediate, are disclosed. Such cells can be eukaryotic or prokaryotic cells, such as yeast cells, plant cells, fungal cells, or bacterial cells such as *Lactobacillus*, *Lactococcus*, *Bacillus*, or *Escherichia* cells. A particular example of such cells were deposited with the American Type Culture Collection (Manassas, Va.) on Dec. 6, 2004 (Accession No. PTA-6411). In one example, the cell is transformed with a BAPAT nucleic acid sequence that confers to the transformed cells BAPAT activity.

One aspect of the disclosure provides transformed cells, which in addition to BAPAT activity (EC 2.1.6.18), include other enzyme activities, such as 3-hydroxypropionate dehydrogenase activity (EC 1.1.1.59), lipase or esterase activity (EC 3.1.1.-), aldehyde dehydrogenase activity (EC 1.2.1.-), alcohol dehydrogenase activity (EC 1.1.1.1), or combinations thereof. In particular examples, the cell can further include alanine 2,3-aminomutase activity. Accordingly, the disclosure also provides methods of producing one or more of these products. These methods involve culturing the cell that includes 3-hydroxypropionate dehydrogenase activity, lipase or esterase activity, alanine 2,3-aminomutase activity, aldehyde dehydrogenase activity, alcohol dehydrogenase activity, or combinations thereof, under conditions that allow the product to be produced.

The disclosed cells can be used to produce nucleic acid molecules, peptides, and organic compounds. In one example the disclosed cells are used in a culture system to produce large quantities of 3-HP and derivatives thereof such as 1,3-propanediol, polymerized 3-HP, co-polymers of 3-HP, and esters of 3-HP. 3-HP is both biologically and commercially important. For example, the nutritional industry can use 3-HP as a food, feed additive or preservative, while the derivatives mentioned above can be produced from 3-HP.

A production cell having at least one exogenous nucleic acid encoding a beta-alanine/pyruvate aminotransferase, is disclosed. Such production cells can be used to produce 3-HP or derivatives thereof. In one example, the nucleic acid sequence includes SEQ ID NO: 17 or 19 (or fragments, variants, or fusions thereof that retain BAPAT activity). Production cells can be used to express peptides that have an enzymatic activity, such as beta-alanine/pyruvate aminotransferase, 3-hydroxypropionate dehydrogenase activity, lipase or esterase activity, alanine 2,3-aminomutase activity, aldehyde dehydrogenase activity, alcohol dehydrogenase activity, or combinations thereof. Methods of producing peptides encoded by the nucleic acid sequences described above are disclosed.

Several methods of producing 3-HP from beta-alanine using the disclosed cells having BAPAT activity are disclosed. In one example, the cell is transfected with one or more enzymes necessary to convert 3-HP from beta-alanine. In another example, the method includes purifying beta-alanine from the cell, then contacting the beta-alanine with peptides necessary to convert 3-HP from beta-alanine.

In some examples, products are produced in vitro (outside of a cell). In other examples, products are produced using a combination of in vitro and in vivo (within a cell) methods. In yet other examples, products are produced in vivo. For methods involving in vivo steps, the cells can be isolated cultured cells or whole organisms such as transgenic plants or single-celled organisms such as yeast and bacteria. Such cells are referred to as production cells. Products produced by these production cells can be organic products such as 3-HP and derivatives thereof such as an ester of 3-HP, polymerized 3-HP, or 1,3-propanediol.

Recombinant nucleic acids that can be used to generate the production cells and practice the methods disclosed herein are provided. For example, operons including two or more nucleic acid sequences, such as two, three, four, five, six, or even seven sequences, each encoding a peptide needed for the production of 3-HP from beta-alanine are disclosed. In a particular example, the recombinant nucleic acid sequence includes a sequence encoding a beta-alanine/pyruvate aminotransferase and a nucleic acid sequence encoding a dehydrogenase capable of converting malonate semialdehyde to 3-HP, such as 3-hydroxypropionate dehydrogenase. Such recombinant nucleic acid sequences can further include a nucleic acid sequence that encodes an alanine 2,3-aminomutase, lipase or esterase, aldehyde dehydrogenase, alcohol dehydrogenase, or combinations thereof. In addition, recombinant nucleic acid sequences can additionally include one or more promoter sequences to drive expression of the coding sequence. The disclosed nucleic acids can be incorporated into a vector, which can be used to transform a cell, or be incorporated into the genome of the cell, or both.

BRIEF DESCRIPTION OF THE FIGURE

FIG. 1 is a diagram of a pathway for generating 3-HP and derivatives thereof via beta-alanine.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NOS: 1 and 2 are PCR primers used to PCR amplify a CAT gene.

SEQ ID NOS: 3 and 4 are PCR primers used to confirm insertion of a CAT gene into the ldhA locus.

SEQ ID NOS: 5 and 6 are PCR primers used to PCR amplify a beta-alanine/pyruvate aminotransferase gene from P. aeruginosa.

SEQ ID NOS: 7 and 8 are PCR primers used to PCR amplify a P. putida beta-alanine/pyruvate aminotransferase gene.

SEQ ID NOS: 9 and 10 are PCR primers used to PCR amplify an mmsB gene from P. aeruginosa.

SEQ ID NOS: 11 and 12 are PCR primers used to PCR amplify an mmsB gene from pET28-mmsB.

SEQ ID NOS: 13 and 14 are PCR primers used to PCR amplify an alanine 2,3-aminomutase gene.

SEQ ID NOS: 15 and 16 are PCR primers used to PCR amplify a P. putida beta-alanine/pyruvate aminotransferase gene from pPRO-PpBAPAT.

SEQ ID NO: 17 is a nucleic acid sequence of a beta-alanine/pyruvate aminotransferase DNA from P. putida.

SEQ ID NO: 18 is an amino acid sequence encoded by SEQ ID NO: 17.

SEQ ID NO: 19 is a nucleic acid sequence of a beta-alanine/pyruvate aminotransferase DNA from Pseudomonas aeruginosa.

SEQ ID NO: 20 is an amino acid sequence encoded by SEQ ID NO: 19.

SEQ ID NOS: 21, 23, and 25 are alanine 2,3-aminomutase nucleic acid sequences. The corresponding amino acid sequences are shown in SEQ ID NOS: 22, 24 and 26, respectively.

SEQ ID NO: 27 is a nucleic acid sequence of a 3-hydroxypropionate/3-hydroxyisobutyrate dehydrogenase (mmsB) DNA.

SEQ ID NO: 28 is an amino acid sequence encoded by SEQ ID NO: 27.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "or" refers to a single element of stated alternative elements or a combination of two or more elements, unless the context clearly indicates otherwise. For example, the phrase "lipase activity or esterase activity" refers to lipase activity, esterase activity, or a combination of both lipase activity and esterase activity.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

Alanine 2,3-aminomutase: An enzyme which can convert alpha-alanine to beta-alanine, for example in a cell. Includes any alanine 2,3-aminomutase gene, cDNA, RNA, or protein from any organism, such as a prokaryote. In particular examples, an alanine 2,3-aminomutase nucleic acid sequence includes the sequence shown in SEQ ID NOS: 21, 23 or 25, as well as fragments, variants, or fusions thereof that retain the ability to encode a protein having alanine 2,3-aminomutase activity. In another example, an alanine 2,3-aminomutase protein includes the amino acid sequence shown in SEQ ID NO: 22, 24 or 26, as well as fragments, fusions, or variants thereof that retain alanine 2,3-aminomutase activity.

An alanine 2,3-aminomutase amino acid sequence includes a full-length sequence, such as SEQ ID NO: 22, 24 or 26, as well as shorter sequences which retain the ability to convert alpha-alanine to beta-alanine, such as amino acids 50-390 of SEQ ID NO: 22 or 24, amino acids 101-339 of SEQ ID NO: 22 or 24, amino acids 15-390 of SEQ ID NO: 26, and amino acids 15-340 of SEQ ID NO 26. This description includes alanine 2,3-aminomutase allelic variants, as well as any variant, fragment, or fusion sequence which retains the ability to convert alpha-alanine to beta-alanine.

Examples of alanine 2,3-aminomutase fragments which can be used include, but are not limited to: amino acids 50-390, 50-350, 60-350, 75-340, or 100-339 of SEQ ID NO: 22 or 24 and amino acids 1-390, 15-390, 15-340 or 19-331 of SEQ ID NO: 26.

Alanine 2,3-aminomutase activity: The ability of an alanine 2,3-aminomutase to convert alpha-alanine to beta-alanine. In one example, such activity occurs in a cell. In another example, such activity occurs in vitro. Such activity can be measured using any assay known in the art. For example, alanine 2,3-aminomutase activity can be identified by incubating the enzyme with either alpha-alanine or beta-alanine and determining the reaction products by high-performance liquid chromatography (for example using the method of Abe et al. *J. Chromatography B*, 712:43-9, 1998).

Examples of substitutions which can be made, while still retaining alanine 2,3-aminomutase activity, include, but are not limited to: V21I or V21L; Y71P; L17I; K361R; A410V; and/or Y430F or Y430W of SEQ ID NO: 22 or 24, and T40S; V96I or V96L; D102E; A252V; or L393V of SEQ ID NO: 26, as well as combinations thereof.

Beta-alanine/pyruvate aminotransferase (BAPAT): An enzyme that can convert beta-alanine and pyruvate to malonate semialdehyde plus alanine. Includes any beta-alanine/pyruvate aminotransferase gene, cDNA, RNA, or protein from any organism, such as a prokaryote or eukaryote. This description includes beta-alanine/pyruvate aminotransferase allelic variants, as well as any variant, fragment, or fusion protein sequence which retains the ability to convert beta-alanine and pyruvate to malonate semialdehyde plus alanine.

Examples include, but are not limited to, any beta-alanine/pyruvate aminotransferase gene, cDNA, RNA, or protein from *Pseudomonas aeruginosa* PAO1 (for example GenBank Accession Nos: AE004451.1 (nucleic acid) and AAG03522 (protein)); *Pseudomonas putida* IFO 14796 (for example GenBank Accession No. P28269 protein); *P. putida* KT2440 (for example GenBank Accession No. NC_002947); *Arabidopsis thaliana* (for example GenBank Accession Nos: AY085348.1 (nucleic acid) and AAM62579 (protein)); rat (for example GenBank Accession Nos: NM_031835 (nucleic acid) and NP_114023 (protein)); and *Xenopus laevis* (for example GenBank Accession No. BE507883).

In particular examples, a beta-alanine/pyruvate aminotransferase nucleic acid sequence includes the sequence shown in SEQ ID NOS: 17 or 19, as well as fragments, variants, or fusions thereof that retain the ability to encode a peptide having beta-alanine/pyruvate aminotransferase activity. In another example, a beta-alanine/pyruvate aminotransferase protein includes the amino acid sequence shown in SEQ ID NO: 18 or 20, as well as fragments, fusions, or variants thereof that retain beta-alanine/pyruvate aminotransferase activity.

Beta-alanine/pyruvate aminotransferase activity. The ability of a beta-alanine/pyruvate aminotransferase to convert beta-alanine and pyruvate to malonate semialdehyde plus alanine. Includes members of EC 2.6.1.18. In one example, such activity occurs in a cell. In another example, such activity occurs in vitro. Such activity can be measured using any assay known in the art. For example, beta-alanine/pyruvate aminotransferase activity can be identified by incubating the enzyme with beta-alanine and pyruvate and determining the reaction products by paper chromatography, amino acid analysis (Yonaha et al., *FEBS Letts.* 71: 21-24, 1976), reaction with an aldehyde-specific reagent (Waters and Venables, *FEMS Microbiol. Letts.* 34: 279-282, 1986), or by coupling the production of malonate semialdehyde to its reduction by a NAD(P)H-dependent 3-HP dehydrogenase and monitoring the change in $A_{340}$.

cDNA (complementary DNA): A piece of DNA lacking internal, non-coding segments (introns) and regulatory sequences which determine transcription. cDNA can be synthesized by reverse transcription from messenger RNA extracted from cells.

Conservative substitution: One or more amino acid substitutions (for example 1, 2, 5 or 10 amino acid residues) for amino acid residues having similar biochemical properties. Typically, conservative substitutions have little to no impact on the activity of a resulting peptide. For example, a conservative substitution is an amino acid substitution in a beta-alanine/pyruvate aminotransferase peptide that does not substantially affect the ability of the peptide to convert beta-alanine to malonate semialdehyde. In a particular example, a conservative substitution is an amino acid substitution in a beta-alanine/pyruvate aminotransferase peptide, such as a conservative substitution in SEQ ID NO: 18 or 20, that does not significantly alter the ability of the protein to convert beta-alanine to malonate semialdehyde, or other downstream products such as 3-HP.

An alanine scan can be used to identify amino acid residues in a beta-alanine/pyruvate aminotransferase peptide that can tolerate substitution. In one example, beta-alanine/pyruvate aminotransferase activity is not altered by more than 25%, for example not more than 20%, for example not more than 10%, when an alanine, or other conservative amino acid (such as those listed below), is substituted for one or more native amino acids.

In a particular example, beta-alanine/pyruvate aminotransferase activity is not substantially altered if the amount of 3-HP produced is not reduced by more than about 25%, such as not more than about 10%, than an amount of 3-HP production in the presence of a beta-alanine/pyruvate aminotransferase containing one or more conservative amino acid substitutions, as compared to an amount of 3-HP production in the presence of a native beta-alanine/pyruvate aminotransferase.

A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly, Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Dehydrogenase: An enzyme that oxidizes a substrate by transferring hydrogen to an acceptor, such as NAD/NADP and also catalyzes the reverse reaction.

Deletion: The removal of a sequence of a nucleic acid, for example DNA, the regions on either side being joined together.

Detectable: Capable of having an existence or presence ascertained. For example, production of 3-HP from beta-alanine is detectable if the signal generated from 3-HP is strong enough to be measured.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. A nucleic acid that is naturally-occurring also can be exogenous to a particular cell. For example, an entire chromosome isolated from cell X is an exogenous nucleic acid with respect to cell Y once that chromosome is introduced into cell Y, even if X and Y are the same cell type.

Functionally Equivalent: Having a similar function. In the context of a beta-alanine/pyruvate aminotransferase molecule, functionally equivalent molecules include different molecules that retain the function of beta-alanine/pyruvate aminotransferase. For example, functional equivalents can be provided by sequence alterations in a beta-alanine/pyruvate aminotransferase, wherein the peptide with one or more sequence alterations retains a function of the unaltered peptide, such that it retains its ability to convert beta-alanine to malonate semialdehyde.

Examples of sequence alterations include, but are not limited to, conservative substitutions, deletions, mutations, frameshifts, and insertions. In one example, a given peptide binds an antibody, and a functional equivalent is a peptide that binds the same antibody. Thus a functional equivalent includes peptides that have the same binding specificity as a peptide, and that can be used as a reagent in place of the peptide (such as in the production of 3-HP and derivatives thereof). In one example a functional equivalent includes a peptide wherein the binding sequence is discontinuous, wherein the antibody binds a linear epitope. Thus, if the peptide sequence is NMPEHAGASL (amino acids 1-10 of SEQ ID NO: 18) a functional equivalent includes discontinuous epitopes, that can appear as follows (=any number of intervening amino acids): $NH_2$--NMPEHAGAS**L-COOH. In this example, the peptide is functionally equivalent to amino acids 1-10 of SEQ ID NO: 18 if the three dimensional structure of the peptide is such that it can bind a monoclonal antibody that binds amino acids 1-10 of SEQ ID NO: 18.

Hybridization: To form base pairs between complementary regions of two strands of DNA, RNA, or between DNA and RNA, thereby forming a duplex molecule. Nucleic acid hybridization techniques can be used to identify an isolated nucleic acid molecule within the scope of the disclosure. Briefly, a nucleic acid molecule having some homology to nucleic acid molecules encoding one of the disclosed enzymes (such as homology to SEQ ID NOS: 17, 19, 21, or variants, fusions, or fragments thereof) can be used as a probe to identify a similar nucleic acid molecule by hybridization under conditions of moderate to high stringency. Once identified, the nucleic acid molecule then can be purified, sequenced, and analyzed to determine if it has the desired enzyme activity, such as BAPAT activity.

Hybridization can be done by Southern or Northern analysis to identify a DNA or RNA sequence, respectively, that hybridizes to a probe. The probe can be labeled, for example with a biotin, a fluorophore, digoxygenin, an enzyme, or a radioisotope such as $^{32}P$. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe including 20 contiguous nucleotides of a beta-alanine/pyruvate aminotransferase (such as 20 contiguous nucleotides of SEQ ID NO:17 or 19) can be used to identify an identical or similar nucleic acid. Probes longer or shorter than 20 nucleotides can also be used.

The disclosure also provides isolated nucleic acid sequences that are at least about 12 bases in length (such as at least about 13, 14, 15, 16, 17, 18, 19, 20, 25, 30, 40, 50, 60, 100, 250, 500, 750, 1000, 1400, 2000, 3000, 4000, or 5000 bases in length) and hybridize, under hybridization conditions, to the sense or antisense strand of an enzyme disclosed herein. The hybridization conditions can be moderately or highly stringent hybridization conditions.

Moderately stringent hybridization conditions are when the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% dextran sulfate, and 1-15 ng/mL probe (about $5×10^7$ cpm/µg), while the washes are performed at about 50° C. with a wash solution containing 2×SSC and 0.1% sodium dodecyl sulfate (SDS).

Highly stringent hybridization conditions are when the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% dextran sulfate, and 1-15 ng/mL probe (about $5×10^7$ cpm/µg), while the washes are performed at about 65° C. with a wash solution containing 0.2×SSC and 0.1% SDS.

3-hydroxypropionate dehydrogenase: An enzyme that can convert malonate semialdehyde to 3-HP. Includes any 3-hydroxypropionate dehydrogenase gene, cDNA, RNA, or protein from any organism, such as a prokaryote or eukaryote. This description includes 3-hydroxypropionate dehydrogenase allelic variants, as well as any variant, fragment, or fusion protein sequence that retains the ability to convert malonate semialdehyde to 3-HP.

Examples include, but are not limited to any gene, cDNA, RNA, or protein from *Pseudomonas aeruginosa* encoding 3-hydroxypropionate dehydrogenase (mmsB gene, see Example 5). In particular examples, a mmsB nucleic acid sequence includes the sequence shown in SEQ ID NO: 27, as well as fragments, variants, or fusions thereof that retain the ability to encode a peptide having 3-hydroxypropionate dehydrogenase activity. In another example, a mmsB protein includes the amino acid sequence shown in SEQ ID NO: 28, as well as fragments, fusions, or variants thereof that retain 3-hydroxypropionate dehydrogenase activity.

3-hydroxypropionate dehydrogenase activity: The ability of a 3-hydroxypropionate dehydrogenase to convert malonate semialdehyde to 3-HP. In one example, such activity occurs in a cell. In another example, such activity occurs in vitro. Such activity can be measured using any assay known in the art. For example, 3-hydroxypropionate dehydrogenase activity can be identified by incubating the enzyme with malonate semialdehyde plus NADH or NADPH and measuring the consumption of NADH or NADPH by monitoring the decrease in absorbance at 340 nm.

Isolated: An "isolated" biological component (such as a nucleic acid molecule or protein) has been substantially separated or purified away from other biological components in the cell of the organism in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules, proteins and peptides.

In one example, isolated refers to a naturally-occurring nucleic acid molecule that is not immediately contiguous with both of the sequences with which it is immediately contiguous (one on the 5' end and one on the 3' end) in the naturally-occurring genome of the organism from which it is derived. For example, an isolated nucleic acid molecule can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (for example, a cDNA or a genomic DNA fragment produced by PCR or restriction endonuclease treatment) independent of other sequences as well as recombinant DNA that is incorporated into a vector, an autonomously replicating plasmid, a virus (for example, a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

In one example, the term "isolated" as used with reference to a nucleic acid molecule also includes any non-naturally-occurring nucleic acid molecule since non-naturally-occurring nucleic acid sequences are not found in nature and do not have immediately contiguous sequences in a naturally-occurring genome. For example, non-naturally-occurring nucleic acid molecules such as an engineered nucleic acid molecule is considered to be an isolated nucleic acid molecule. Engineered nucleic acid molecules can be made using common molecular cloning or chemical nucleic acid synthesis techniques. Isolated non-naturally-occurring nucleic acid molecule can be independent of other sequences, or incorporated into a vector, an autonomously replicating plasmid, a virus (such as a retrovirus, adenovirus, or herpes virus), or the genomic DNA of a prokaryote or eukaryote. In addition, a non-naturally-occurring nucleic acid molecule can include a nucleic acid molecule that is part of a hybrid or fusion nucleic acid sequence.

Nucleic acid molecule: Encompasses both RNA and DNA including, without limitation, cDNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

Oligonucleotide: A linear polynucleotide (such as DNA or RNA) sequence of at least 9 nucleotides, for example at least 12, 15, 18, 20, 25, 30, 50, 100 or even 200 nucleotides long. In one example, an oligonucleotide is no more than 100 nucleotides in length, such as no more than 50 nucleotides, such as no more than 25 nucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, for example in a plasmid vector, under the transcriptional regulation of a single promoter, constitutes a synthetic operon.

ORF (open reading frame): A series of nucleotide triplets (codons) coding for amino acids without any termination codons. These sequences are usually translatable into a peptide.

Probes and primers: A "probe" includes an isolated nucleic acid molecule containing a detectable label or reporter molecule. Exemplary labels include radioactive isotopes, ligands, chemiluminescent agents, fluorophores, and enzymes. Methods for labeling and guidance in the choice of labels appropriate for various purposes are discussed in, for example, Sambrook et al. (ed.), Molecular Cloning: A Laboratory Manual 2nd ed., vol. 1-3, Cold Spring Harbor Laboratory Press, Cold Spring Harbor, N.Y., 1989, and Ausubel et al. (ed.) Current Protocols in Molecular Biology, Greene Publishing and Wiley-Interscience, New York (with periodic updates), 1987.

"Primers" are typically nucleic acid molecules having ten or more nucleotides (such as nucleic acid molecules having between about 10 nucleotides and about 100 nucleotides). A primer can be annealed to a complementary target nucleic acid strand by nucleic acid hybridization to form a hybrid between the primer and the target nucleic acid strand, and then extended along the target nucleic acid strand by, for example, a DNA polymerase enzyme. Primer pairs can be used for amplification of a nucleic acid sequence, for example, by the polymerase chain reaction (PCR) or other nucleic-acid amplification methods.

Methods for preparing and using probes and primers are described, for example, in references such as Sambrook et al. (ed.), Molecular Cloning: A Laboratory Manual, 2nd ed., vol. 1-3, Cold Spring Harbor Laboratory Press, Cold Spring Harbor, N.Y., 1989; Ausubel et al. (ed.), Current Protocols in Molecular Biology, Greene Publishing and Wiley-Interscience, New York (with periodic updates), 1987; and Innis et al., PCR Protocols: A Guide to Methods and Applications, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.).

One of skill in the art will appreciate that the specificity of a particular probe or primer increases with the length, but that a probe or primer can range in size from a full-length sequence to sequences as short as five consecutive nucleotides. Thus, for example, a primer of 20 consecutive nucleotides can anneal to a target with a higher specificity than a corresponding primer of only 15 nucleotides. Thus, in order to obtain greater specificity, probes and primers can be selected that include, for example, 25, 30, 35, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, or more consecutive nucleotides.

Promoter: An array of nucleic acid control sequences which direct transcription of a nucleic acid. A promoter includes necessary nucleic acid sequences near the start site of transcription, such as a TATA element. A promoter also optionally includes distal enhancer or repressor elements which can be located as much as several thousand base pairs from the start site of transcription.

Purified: The term purified does not require absolute purity; rather, it is intended as a relative term. Thus, for example, a purified peptide preparation is one in which the peptide in is more enriched than the peptide is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide.

In one example, a peptide is purified when at least about 50% by weight of a sample is composed of the peptide, for example when at least about 60%, 70%, 80%, 85%, 90%, 92%, 95%, 98%, or 99% or more of a sample is composed of the peptide. Examples of methods that can be used to purify a peptide, include, but are not limited to the methods disclosed in Sambrook et al. (*Molecular Cloning: A Laboratory Manual*, Cold Spring Harbor, N.Y., 1989, Ch. 17). Protein purity can be determined by, for example, polyacrylamide gel electrophoresis of a protein sample, followed by visualization of a single peptide band upon staining the polyacrylamide gel; high-pressure liquid chromatography; sequencing; or other conventional methods.

Recombinant: A recombinant nucleic acid molecule is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules, such as genetic engineering techniques. Recombinant is also used to describe nucleic acid molecules that have been artificially manipulated, but contain the same regulatory sequences and coding regions that are found in the organism from which the nucleic acid was isolated.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

```
                   1                   20
Target   Sequence:AGGTCGTGTACTGTCAGTCA
                  | || ||| |||| |||| |
Identified Sequence:ACGTGGTGAACTGCCAGTGA
```

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity.

When aligning short peptides (fewer than around 30 amino acids), the alignment should be performed using the Blast 2 sequences function, employing the PAM30 matrix set to default parameters (open gap 9; extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity determined by this method. An alternative (and not necessarily cumulative) indication that two nucleic acid sequences are substantially identical is that the peptide which the first nucleic acid encodes is immunologically cross reactive with the peptide encoded by the second nucleic acid.

One of skill in the art will appreciate that the particular sequence identity ranges are provided for guidance only; it is possible that strongly significant homologs could be obtained that fall outside the ranges provided.

Transformed cell: A cell into which a nucleic acid molecule has been introduced, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

Variants, fragments or fusion proteins: The enzymes disclosed herein that can be used to produce 3-HP and derivatives thereof, include variants, fragments, and fusions thereof that retain essentially the same activity as the native enzyme. DNA sequences which encode for an enzyme (for example SEQ ID NO: 17, 19, 21, 23, 25 or 27), or a fusion, fragment or variant thereof, can be engineered to allow the protein to be expressed in a cell, such as a yeast, bacteria, insect, plant, or cell. To obtain expression, the DNA sequence can be altered and operably linked to other regulatory sequences. The final product, which contains the regulatory sequences and the protein, is a vector. This vector can be introduced into any cell, such as a eukaryotic, bacteria, insect, or plant cell. Once inside the cell the vector allows the protein to be produced.

A fusion protein including an enzyme, such as an enzyme used to produce 3-HP (or variant, polymorphism, mutant, or fragment thereof), linked to other amino acid sequences that do not inhibit the desired activity of the enzyme, for example the ability to convert beta-alanine to 3-HP. In one example, the other amino acid sequences are no more than about 10, 12, 15, 20, 25, 30, or 50 amino acids in length.

One of ordinary skill in the art will appreciate that a DNA sequence can be altered in numerous ways without affecting the biological activity of the encoded protein. For example, PCR can be used to produce variations in the DNA sequence which encodes an enzyme. Such variants can be variants optimized for codon preference in a host cell used to express the protein, or other sequence changes that facilitate expression.

Vector: A nucleic acid molecule as introduced into a cell, thereby producing a transformed cell. A vector can include nucleic acid sequences that permit it to replicate in the cell, such as an origin of replication. In particular examples, a vector also includes one or more selectable markers or other genetic elements. A vector can also be nonreplicating, such that it is a means of introducing nucleic acid sequences that are integrated into the genome of the cell.

Cells to Produce 3-HP and 3-HP Derivatives

Transformed cells having beta-alanine/pyruvate aminotransferase activity (EC 2.6.1.18) are disclosed. Such cells can produce 3-HP from beta-alanine and pyruvate via a malonate semialdehyde intermediate. Transformed cells including beta-alanine/pyruvate aminotransferase activity can be eukaryotic or prokaryotic. Examples of such cells include, but are not limited to *Lactobacillus, Lactococcus, Bacillus, Escherichia, Geobacillus, Corynebacterium, Clostridium*, fungal, plant, and yeast cells. In one example, a plant cell is part of a plant, such as a transgenic plant. Transformed cells can include at least one exogenous nucleic acid molecule that encodes a beta-alanine/pyruvate aminotransferase (EC 2.6.1.18), for example a sequence including SEQ ID NO: 17 or 19, or variants, fragments, or fusions thereof that retain the ability to convert beta-alanine to malonate semialdehyde. The disclosed transformed cells can further include other exogenous nucleic acid molecules that encode other enzymes, such as 3-hydroxypropionate dehydrogenase (EC 1.1.1.59), alanine 2,3-aminomutase, lipase or esterase (EC 3.1.1.-), aldehyde dehydrogenase (EC 1.2.1.-), alcohol dehydrogenase (EC 1.1.1.1), or combinations thereof.

Cells that include beta-alanine/pyruvate aminotransferase activity, as well as additional enzyme activities, are disclosed. In one example, transformed cells having beta-alanine/pyruvate aminotransferase activity also have dehydrogenase activity, such as an enzyme capable of converting malonate semialdehyde to 3-HP, for example 3-hydroxypropionate dehydrogenase activity. One non-limiting example of an enzyme having 3-hydroxypropionate dehydrogenase activity is an mmsB enzyme from *P. aeruginosa* (such as SEQ ID NO: 28 and variants, fusions, and fragments thereof that retain 3-hydroxypropionate dehydrogenase activity).

In another example, transformed cells having beta-alanine/pyruvate aminotransferase activity and 3-hydroxypropionate dehydrogenase activity also have alanine 2,3-aminomutase activity. Non-limiting examples of an enzyme having alanine 2,3-aminomutase activity include SEQ ID NO: 22, 24 and 26, and variants, fusions, and fragments thereof that retain alanine 2,3-aminomutase activity. In a particular example, a transformed cell includes beta-alanine/pyruvate aminotransferase activity, 3-hydroxypropionate dehydrogenase activity, alanine 2,3-aminomutase activity, as well as lipase or esterase activity, or a combination of both lipase activity and esterase activity. Such transformed cells can be used to produce an ester of 3-HP, such as methyl 3-hydroxypropionate, ethyl 3-hydroxypropionate, propyl 3-hydroxypropionate, butyl 3-hydroxypropionate, or 2-ethylhexyl 3-hydroxypropionate.

In another example, transformed cells having beta-alanine/pyruvate aminotransferase activity also include aldehyde dehydrogenase activity and alcohol dehydrogenase activity. These cells can be used to produce 1,3-propanediol. In some examples, such cells further include 3-hydroxypropionate dehydrogenase activity, alanine 2,3-aminomutase activity, or a combination of both 3-hydroxypropionate dehydrogenase activity and alanine 2,3-aminomutase activity.

In a particular example, transformed cells having beta-alanine/pyruvate aminotransferase activity also include esterase activity. These cells can be used to produce polymerized 3-HP. In some examples, such cells further include 3-hydroxypropionate dehydrogenase activity, alanine 2,3-aminomutase activity, or a combination of both 3-hydroxypropionate dehydrogenase activity and alanine 2,3-aminomutase activity.

Pathways for Producing 3-HP and Derivatives Thereof

Provided herein are methods for producing 3-HP from beta-alanine by using a beta-alanine/pyruvate aminotransferase. Several beta-alanine/pyruvate aminotransferase sequences and cells having beta-alanine/pyruvate aminotransferase activity, are disclosed. In addition, methods and materials related to producing esters of 3-HP, polymers of 3-HP, and 1,3-propanediol are provided.

Specifically, the disclosure provides a novel route for producing 3-HP from beta-alanine using beta-alanine/pyruvate aminotransferase nucleic acids (such as SEQ ID NO: 17, 19 and variants, fragments and fusions thereof), peptides (such as SEQ ID NO: 18, 20 and variants, fragments and fusions thereof), which is more efficient and allows for the production of greater amounts of 3-HP as well as derivatives thereof such as 1,3-propanediol, polymerized 3-HP, and esters of 3-HP.

Pathways of 3-HP and its Derivatives

As shown in FIG. 1, beta-alanine can be converted into malonate semialdehyde through the use of a peptide having beta-alanine/pyruvate aminotransferase activity (E.C. 2.6.1.18). Exemplary beta-alanine/pyruvate aminotransferases include, but are not limited to sequences including SEQ ID NOS: 18 and 20, or fragments, variants, or fusions thereof that retain beta-alanine/pyruvate aminotransferase activity. Beta-alanine can be produced from aspartic acid by aspartate decarboxylase. Beta-alanine can also be produced from alpha-alanine by endogenous peptides in a host cell that converts alpha-alanine to beta-alanine. Beta-alanine can also be produced from alanine by alanine-2,3-aminomutase which converts alpha-alanine to beta-alanine. For example, a cell transformed with recombinant alanine 2,3-aminomutase nucleic acid, such as a sequence including SEQ ID NO: 21, 23, or 25, or fragments, variants, or fusions thereof that retain alanine 2,3-aminomutase activity, can be used to produce beta-alanine.

Malonate semialdehyde produced from beta-alanine can then be converted into 3-HP through the use of a 3-HP dehydrogenase, such as a 3-hydroxypropionate dehydrogenase. Exemplary 3-hydroxypropionate dehydrogenases include, but are not limited to sequences including SEQ ID NO: 28, or fragments, variants, or fusions thereof that retain 3-hydroxypropionate dehydrogenase activity.

Derivatives of 3-HP can be made from beta-alanine as shown in FIG. 1. For example, the resulting 3-HP can be converted into an ester of 3-HP by a peptide having lipase or esterase activity, or a combination thereof (EC 3.1.1.-). In addition, the resulting 3-HP can be converted into a polymerized 3-HP by a peptide having esterase activity.

The resulting 3-HP can also be converted into 1,3-propanediol by a peptide having aldehyde dehydrogenase activity (EC 1.2.1.-) and a peptide having alcohol dehydrogenase activity (EC 1.1.1.1). In addition, 1,3-propanediol can be generated using peptides having oxidoreductase activity (such as enzymes in the 1.1.1.-class of enzymes) in vitro or in vivo. The formation of 1,3-propanediol during fermentation or in an in vitro assay can be analyzed using a High Performance Liquid Chromatography (HPLC). The chromatographic separation can be achieved by using a Bio-Rad 87H ion-exchange column. A mobile phase of 0.01N sulfuric acid is passed at a flow rate of 0.6 ml/min and the column maintained at a temperature of 45-65° C. The presence of 1,3-propanediol in the sample can be detected using a refractive index detector (Skraly et al., *Appl. Environ. Microbiol.* 64:98-105, 1998).

In another example, 3-HP can be dehydrated to form acrylic acid. Any method can be used to perform a dehydration reaction. For example, 3-HP can be heated in the presence of a catalyst (such as a metal or mineral acid catalyst) to form acrylic acid.

Enzymes

Peptides having beta-alanine/pyruvate aminotransferase activity, as well as nucleic acid molecules encoding such peptides, can be obtained from various species including, but not limited to: *Pseudomonas putida, Pseudomonas aeruginosa, Arabidopsis thaliana, Rattus norvegicus*, and *Xenopus laevis*. For example, nucleic acid sequences having beta-alanine/pyruvate aminotransferase are shown in SEQ ID NO: 17 for *Pseudomonas putida* (the corresponding amino acid sequence is shown in SEQ ID NO: 18), and in SEQ ID NO: 19 for *Pseudomonas aeruginosa* (the corresponding amino acid sequence is shown in SEQ ID NO: 20). In addition, other peptides having beta-alanine/pyruvate aminotransferase as well as nucleic acid molecules encoding such peptides, can be obtained using the methods described herein. For example, beta-alanine/pyruvate aminotransferase variants having beta-alanine/pyruvate aminotransferase activity can be used.

Peptides having alanine 2,3-aminomutase activity, as well as nucleic acid molecules encoding such peptides, can be obtained from various species including, but not limited to: *Bacillus subtilis, Porphyromonas gingivalis, Clostridium*

*sticklandii*, or *Fusobacterium nucleatum*. For example, nucleic acid sequences having alanine 2,3-aminomutase activity are shown in SEQ ID NO: 21 and 23 for *B. subtilis* (the corresponding amino acid sequences are shown in SEQ ID NO: 22 and 24, respectively), and in SEQ ID NO: 25 for *P. gingivalis* (the corresponding amino acid sequence is shown in SEQ ID NO: 26). Alanine 2,3-aminomutase variants having alanine 2,3-aminomutase activity can also be used.

Peptides having 3-hydroxypropionate dehydrogenase activity (EC 1.1.1.59), such as that encoded by the mmsB gene of *Pseudomonas aeruginosa*, as well as nucleic acid molecules encoding such peptides, can be obtained from various species. For example, a nucleic acid molecule that encodes a peptide having 3-hydroxypropionate dehydrogenase activity is shown in SEQ ID NO: 27 (see also GenBank Accession No: AE004778 (for protein, see GenBank Accession No: AAG06957) and GenBank Accession No: M84911 (for protein, see GenBank Accession No: AAA25891)).

Peptides having lipase or esterase activity as well as nucleic acid molecules encoding such peptides can be obtained from various species including, without limitation, *Candida rugosa, Candida tropicalis,* and *Candida albicans*. For example, nucleic acid molecules that encode a peptide having lipase activity can be obtained from *C. rugosa* and can have a sequence as set forth in GenBank accession number A81171 (PCT Publication No. WO/9914338).

Peptides having aldehyde dehydrogenase (NAD(P)+) (EC 1.2.1.-) activity as well as nucleic acid molecules encoding such peptides can be obtained from various species including, without limitation, *S. cerevisiae*. For example, nucleic acid molecules that encode a peptide having aldehyde dehydrogenase activity can be obtained from *S. cerevisiae* and can have a sequence as set forth in GenBank Accession No. Z75282 (Tessier et al. *FEMS Microbiol. Lett.* 164:29-34, 1998).

Peptides having alcohol dehydrogenase activity (EC 1.1.1.1) as well as nucleic acid molecules encoding such peptides can be obtained from various species including, without limitation, *Z. mobilis*. For example, a nucleic acid molecule that encodes a peptide having alcohol dehydrogenase activity can be obtained from *Z. mobilis* and can have a sequence as set forth in GenBank accession No. M32100.

The term "peptide having enzymatic activity" refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as beta-alanine/pyruvate aminotransferase, dehydrogenases capable of converting malonate semialdehyde to 3-HP such as 3-hydroxypropionate dehydrogenase, alanine 2,3-aminomutase, lipase or esterase, aldehyde dehydrogenase, and alcohol dehydrogenase.

Methods of Making 3-HP and Derivatives Thereof

Each step provided in the pathways depicted in FIG. 1 can be performed within a cell (in vivo) or outside a cell (in vitro, for example in a container or column). Additionally, the organic compound products can be generated through a combination of in vivo synthesis and in vitro synthesis. Moreover, the in vitro synthesis step, or steps, can be via chemical reaction or enzymatic reaction.

For example, a cell or microorganism provided herein can be used to perform the steps provided in FIG. 1, or an extract containing peptides having the indicated enzymatic activities can be used to perform the steps provided in FIG. 1. In addition, chemical treatments can be used to perform the conversions provided in FIG. 1.

Expression of Peptides

The peptides described herein, such as the enzymes listed in FIG. 1, can be produced individually in a host cell or in combination in a host cell. Moreover, the peptides having a particular enzymatic activity can be a peptide that is either naturally-occurring or non-naturally-occurring. A naturally-occurring peptide is any peptide having an amino acid sequence as found in nature, including wild-type and polymorphic peptides. Naturally-occurring peptides can be obtained from any species including, but not limited to, animal (such as mammalian), plant, fungal, and bacterial species. A non-naturally-occurring peptide is any peptide having an amino acid sequence that is not found in nature. Thus, a non-naturally-occurring peptide can be a mutated version of a naturally-occurring peptide, or an engineered peptide. A peptide can be mutated by, for example, sequence additions, deletions, substitutions, or combinations thereof.

Genetically modified cells are disclosed which can be used to perform one or more steps of the steps in the pathways described herein or the genetically modified cells can be used to produce the disclosed peptides for subsequent use in vitro. For example, an individual microorganism can contain one or more exogenous nucleic acids encoding each peptide to perform the steps depicted in FIG. 1. Such cells can contain any number of exogenous nucleic acid molecules. For example, a particular cell can contain one, two, three, four, five, six, or seven, or even more different exogenous nucleic acid molecules with each one encoding a peptide for converting beta-alanine into 3-HP as shown in FIG. 1, or a particular cell can endogenously produce peptides for converting malonate semialdehyde into 3-HP while containing an exogenous nucleic acid molecule that encodes peptides for converting beta-alanine into malonate semialdehyde and in some examples an exogenous nucleic acid molecule that encodes peptides that can convert alpha-alanine into beta-alanine.

In addition, a single exogenous nucleic acid molecule can encode one, or more than one, peptide. For example, a single exogenous nucleic acid molecule can include sequences that encode two, three, four, five, six, seven, or even more different peptides. Further, the cells described herein can contain a single copy, or multiple copies (such as about 5, 10, 20, 35, 50, 75, 100 or 150 copies), of a particular exogenous nucleic acid molecule, such as a particular enzyme. The cells described herein can contain more than one particular exogenous nucleic acid sequence. For example, a particular cell can contain about 50 copies of exogenous nucleic acid molecule X as well as about 75 copies of exogenous nucleic acid molecule Y.

In one example, a cell includes an exogenous nucleic acid molecule that encodes a peptide having BAPAT activity, for example SEQ ID NO: 17 or 19 (or variants, fragments, or fusions thereof that retain BAPAT activity). Such cells can have any detectable level of BAPAT activity, including activity detected by the production of metabolites of beta-alanine. For example, a cell containing an exogenous nucleic acid molecule that encodes a peptide having BAPAT activity can have BAPAT activity with a specific activity greater than about 1 μg malonate semialdehyde formed per gram dry cell weight per hour (for example greater than about 10, 20, 30, 40, 50, 60, 70, 80, 90, 100, 125, 150, 200, 250, 300, 350, 400, 500, or more μg malonate semialdehyde formed per gram dry cell weight per hour). Alternatively, a cell can have BAPAT activity such that a cell extract from $1 \times 10^6$ cells has a specific activity greater than about 1 ng malonate semialdehyde formed per mg total protein per minute (such as greater than about 10, 20, 30, 40, 50, 60, 70, 80, 90, 100, 125, 150, 200, 250, 300, 350, 400, 500, or more ng 3-HP formed per mg total protein per minute).

Host Cells for Production of 3-HP and Related Products

The nucleic acid and amino acid sequences provided herein can be used with cells to produce 3-HP as well as derivatives thereof such as esters of 3-HP, polymerized 3-HP and 1,3-propanediol, for example using the pathways shown in Example 1. Such cells can be from any species, such as those listed within the taxonomy web pages at the National Institutes of Health. The cells can be eukaryotic or prokaryotic. For example, genetically modified cells can be mammalian cells (such as human, murine, and bovine cells), plant cells (such as corn, wheat, rice, and soybean cells), fungal cells (such as *Aspergillus* and *Rhizopus* cells), yeast cells, or bacterial cells (such as *Lactobacillus, Lactococcus, Bacillus, Escherichia,* and *Clostridium* cells).

In one example, a cell is a microorganism. The term "microorganism" refers to any microscopic organism including, but not limited to, bacteria, algae, fungi, and protozoa. Thus, *E. coli, B. subtilis, B. licheniformis, S. cerevisiae, Kluveromyces lactis, Candida blankii, Candida rugosa,* and *Pichia pastoris* are microorganisms and can be used as described herein. In another example, the cell is part of a larger organism, such as a plant, such as a transgenic plant. Examples of plants that can be used to make 3-HP or other organic compounds from beta-alanine include, but are not limited to, genetically engineered plant crops such as corn, rice, wheat, and soybean.

In one example, cells that are genetically modified to synthesize a particular organic compound contain one or more exogenous nucleic acid molecules that encode peptides having specific enzymatic activities. For example, a microorganism can contain exogenous nucleic acid that encodes a peptide having BAPAT activity. In this case, beta-alanine can be converted into malonate semialdehyde, which can lead to the production of 3-HP. An exogenous nucleic acid molecule that encodes a peptide having an enzymatic activity that catalyzes the production of a compound not normally produced by a cell, can be introduced into the cell. Alternatively, a cell can be transformed with an exogenous nucleic acid molecule that encodes a peptide having an enzymatic activity that catalyzes the production of a compound that is normally produced by that cell. In this case, the genetically modified cell can produce more of the compound (such as 3-HP, derivatives thereof, or a combination of 3-HP and its derivatives), or can produce the compound more efficiently, than a similar cell not having the genetic modification.

The produced one or more products can be secreted from the cell, eliminating the need to disrupt cell membranes to retrieve the organic compound. In one example, the cell produces 3-HP, derivatives thereof, or both, with the concentration of the one or more products being at least about 1 mg per L (such as at least about 1 mg/L, 5 mg/L, 10 mg/L, 25 mg/L, –100 mg/L, 500 mg/L, 1 g/L, 5 g/L, 10 g/L, 25 g/L, 50 g/L, 100 g/L or 150 g/L). When determining the yield of a compound such as 3-HP or derivatives thereof for a particular cell, any method can be used (such as *Applied Environmental Microbiology* 59(12):4261-5, 1993). A cell within the scope of the disclosure can utilize a variety of carbon sources.

A cell can contain one or more exogenous nucleic acid molecules that encodes one or more peptides having enzymatic activity that leads to the formation of 3-HP or derivatives thereof, such as 1,3-propanediol, 3-HP-esters, and polymers and copolymers containing 3-HP. Methods of identifying cells that contain exogenous nucleic acid molecules are well known. Such methods include, without limitation, PCR and nucleic acid hybridization techniques such as Northern and Southern analysis (see hybridization described herein). In addition, immunohisto-chemical and biochemical techniques can be used to determine if a cell contains a particular nucleic acid sequence by detecting the expression of the peptide encoded by that particular nucleic acid molecule. For example, an antibody having specificity for a peptide can be used to determine whether or not a particular cell contains a nucleic acid molecule encoding that peptide.

Biochemical techniques can also be used to determine if a cell contains a particular nucleic acid molecule encoding a peptide having enzymatic activity by detecting an organic product produced as a result of the expression of the peptide having enzymatic activity. For example, detection of 3-HP after introduction of one or more exogenous nucleic acid molecules that encode a peptide having BAPAT activity (and in some examples also introducing an exogenous nucleic acid molecule encoding a peptide having 3-hydroxypropionate dehydrogenase activity) into a cell that does not normally express such a peptide can indicate that the cell not only contains the introduced exogenous nucleic acid molecule but also expresses the encoded peptide from that introduced exogenous nucleic acid molecule.

Methods for detecting specific enzymatic activities or the presence of particular organic products are well known, for example, the presence of an organic compound such as 3-HP can be determined as described in Sullivan and Clarke (*J. Assoc. Offic. Agr. Chemists,* 38:514-8, 1955).

Operons for Producing 3-HP and Derivatives Thereof

Operons including more than one coding sequence are disclosed. In one example, the operon includes a nucleic acid sequence encoding a beta-alanine/pyruvate aminotransferase, and a nucleic acid sequence encoding a dehydrogenase capable of converting malonate semialdehyde to 3-HP, such as 3-hydroxypropionate dehydrogenase. In a particular example, the operon further includes a nucleic acid sequence encoding an alanine 2,3-aminomutase. In yet other examples, the operon further includes a nucleic acid sequence encoding a lipase or esterase, or combinations thereof, which can be used to produce 3-HP esters. In another example, the operon further includes a nucleic acid sequence encoding an esterase which can be used to produce polymers of 3-HP. In still other examples, the operon further includes a nucleic acid sequence encoding an alcohol dehydrogenase and an aldehyde dehydrogenase which can be used to produce 1,3-propanediol. These recombinant operons can also include a promoter, to drive expression of the coding sequences. Furthermore, the operons can be part of a vector, which is used to transform a cell that can be used to produce 3-HP or derivatives thereof.

Nucleic Acids and Proteins for Producing 3-HP and Derivatives Thereof

Enzymes that can be used to produce 3-HP and derivatives thereof are disclosed herein. Several exemplary enzyme sequences are disclosed herein; however, the disclosure also encompasses variants, fusions, and fragments of the enzymes that retain the particular enzyme activity.

The nucleic acid sequences encoding the enzymes disclosed herein can contain an entire nucleic acid sequence encoding the enzyme, as well as portions thereof that retain the desired enzyme activity. For example, an enzyme nucleic acid sequence can contain at least about 12 contiguous nucleotides of an enzyme nucleic acid sequence. It will be appreciated that the disclosure also provides isolated nucleic acid that contains a nucleotide sequence that is greater than about 12 nucleotides (such as at least 13, 14, 15, 16, 17, 18, 19, 20, 25, 30, 40, 50, 60, 100, 250, 500, 750, 1000, 1500, 2000, 3000, 4000, or 5000 bases) in length and identical to any portion of an enzyme sequence. The disclosure also provides isolated nucleic acid sequences that encode for an enzyme having at least about 12 bases and hybridizes, under moderately or highly stringent hybridization conditions, to the sense or antisense strand of a nucleic acid sequence encoding the desired enzyme.

In addition, the disclosure provides isolated enzyme nucleic acid sequences which contain a variation of an enzyme sequence. Variants can contain a single insertion, a single deletion, a single substitution, multiple insertions, multiple deletions, multiple substitutions, or any combination thereof (such as a single deletion together with multiple insertions) as long as the peptide encoded thereby retains the appropriate activity. Such isolated nucleic acid molecules can share at least about 60%, 70%, 75%, 80%, 85%, 90%, 92%, 95%, 97%, 98%, or 99% sequence identity with an enzyme sequence, as long as the peptide encoded by the nucleic acid sequence retains the desired enzyme activity. For example, the following variations can be made to an alanine 2,3-aminomutase nucleic acid sequence: for SEQ ID NO: 21 or 23, the "a" at position 12 can be substituted with an "g"; the "g" at position 1050 can be substituted with an "a"; the "a" at position 255; can be substituted with an "g" "t" or "c;" for SEQ ID NO: 25, the "a" at position 6 can be substituted with a "g" "t" or "c"; the "t" at position 66 can be substituted with a "c"; and the "g" at position 315; can be substituted with an "a" "t" or "c." Similarly, the following variations can be made to a beta-alanine/pyruvate aminotransferase nucleic acid sequence: for SEQ ID NO: 17, the "c" at position 12 can be substituted with a "g" "t" or "a"; the "t" at position 336 can be substituted with an "c"; the "g" at position 1104 can be substituted with an "a" "t" or "c;" for SEQ ID NO: 19, the "g" at positions 51 and 528 can be substituted with a "a" "t" or "c"; the "c" at position 672 can be substituted with a "t" or an "a"; and the "g" at position 1296; can be substituted with an "a".

Codon preferences and codon usage tables for a particular species can be used to engineer isolated nucleic acid molecules that take advantage of the codon usage preferences of that particular species. For example, the enzymes disclosed herein can be designed to have codons that are preferentially used by a particular organism of interest.

Nucleic acid molecules encoding a peptide can be produced by standard DNA mutagenesis techniques, for example, M13 primer mutagenesis. Details of these techniques are provided in Sambrook et al. (ed.), Molecular Cloning: A Laboratory Manual 2nd ed., vol. 1-3, Cold Spring Harbor Laboratory Press, Cold Spring, Harbor, N.Y., 1989, Ch. 15. Nucleic acid molecules can contain changes of a coding region to fit the codon usage bias of the particular organism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a peptide having an amino acid sequence identical or substantially similar to the native amino acid sequence. For example, because of the degeneracy of the genetic code, alanine is encoded by the four nucleotide codon triplets: GCT, GCA, GCC, and GCG. Thus, the nucleic acid sequence of the open reading frame can be changed at an alanine position to any of these codons without affecting the amino acid sequence of the encoded peptide or the characteristics of the peptide. Based upon the degeneracy of the genetic code, nucleic acid variants can be derived from a nucleic acid sequence using standard DNA mutagenesis techniques as described herein, or by synthesis of nucleic acid sequences. Thus, this disclosure also encompasses nucleic acid molecules that encode the same peptide but vary in nucleic acid sequence by virtue of the degeneracy of the genetic code.

Identification of Alternative Sequences

A nucleic acid molecule encoding a peptide having the desired enzymatic activity can be identified and obtained using any method such as those described herein. For example, nucleic acid molecules that encode a peptide having the desired enzymatic activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known enzymatic peptides. Sequence alignment software such as MEGALIGN (DNASTAR, Madison, Wis., 1997) can be used to compare various sequences.

In addition, nucleic acid molecules encoding known enzymatic peptides can be altered using common molecular cloning techniques (such as site-directed mutagenesis). Possible alterations include, without limitation, deletions, insertions, and substitutions, and combinations thereof. Further, nucleic acid and amino acid databases (such as GenBank and EMBL-EBI) can be used to identify a nucleic acid sequence that encodes a peptide having the desired enzymatic activity. Briefly, any amino acid sequence having some homology to a peptide having enzymatic activity, or any nucleic acid sequence having some homology to a sequence encoding a peptide having enzymatic activity can be used as a query to search GenBank. The identified peptides then can be analyzed to determine whether or not they exhibit enzymatic activity.

In addition, nucleic acid hybridization techniques can be used to identify and obtain a nucleic acid molecule that encodes a peptide having enzymatic activity. Briefly, any nucleic acid molecule that encodes a known enzymatic peptide, or fragment thereof, can be used as a probe to identify similar nucleic acid molecules by hybridization under conditions of moderate to high stringency. Such similar nucleic acid molecules then can be isolated, sequenced, and analyzed to determine whether the encoded peptide has similar enzymatic activity.

Expression cloning techniques also can be used to identify and obtain a nucleic acid molecule that encodes a peptide having the desired enzymatic activity. For example, a substrate known to interact with a particular enzymatic peptide can be used to screen a phage display library containing that enzymatic peptide. Phage display libraries can be generated as described (Burritt et al., *Anal. Biochem.* 238:1-13, 1990), or can be obtained from commercial suppliers such as Novagen (Madison, Wis.).

Further, peptide sequencing techniques can be used to identify and obtain a nucleic acid molecule that encodes a peptide having the desired enzymatic activity. For example, a purified peptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid sequence encoding the peptide by PCR. Once obtained, the nucleic acid molecule can be sequenced, cloned into an appropriate expression vector, and introduced into a microorganism.

Transforming Cells

Any method can be used to introduce an exogenous nucleic acid molecule into a cell. For example, heat shock, lipofection, electroporation, conjugation, fusion of protoplasts, and biolistic delivery are common methods for introducing nucleic acid into bacteria and yeast cells. (for example, see Ito et al., *J. Bacterol.* 153:163-8, 1983; Durrens et al., *Curr. Genet.* 18:7-12, 1990; Sambrook et al., Molecular cloning: A laboratory manual, Cold Spring Harbour Laboratory Press, New York, USA, second edition, 1989; and Becker and Guarente, *Methods in Enzymology* 194:182-7, 1991). Other methods for expressing an amino acid sequence from an exogenous nucleic acid molecule include, but are not limited to, constructing a nucleic acid molecule such that a regulatory element promotes the expression of a nucleic acid sequence that encodes a peptide. Typically, regulatory elements are DNA sequences that regulate the expression of other DNA sequences at the level of transcription. Thus, regulatory elements include, without limitation, promoters, enhancers, and the like.

Any type of promoter can be used to express an amino acid sequence from an exogenous nucleic acid molecule. Examples of promoters include, without limitation, constitutive promoters, tissue-specific promoters, and promoters responsive or unresponsive to a particular stimulus (such as light, oxygen, chemical concentration). Methods for transferring nucleic acids into mammalian cells are also known, such as using viral vectors.

An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant. A microorganism can contain single or multiple copies (such as about 5, 10, 20, 35, 50, 75, 100 or 150 copies), of a particular exogenous nucleic acid molecule, such as a nucleic acid encoding an enzyme.

In Vitro Production of Organic Acids and Related Products

Purified peptides having enzymatic activity can be used alone, or in combination with cells, to produce 3-HP, derivatives thereof, or both, such as esters of 3-HP, polymerized 3-HP, and 1,3-propanediol. Further, cell-free extracts containing a peptide having enzymatic activity can be used alone or in combination with purified peptides, cells, or both, to produce 3-HP, derivatives thereof, or both.

For example, a cell-free extract that includes a peptide having BAPAT activity can be used to form malonate semialdehyde from beta-alanine, while a cell or microorganism containing peptides having the enzymatic activities necessary to catalyze the reactions needed to form 3-HP from malonate semialdehyde can be used to produce 3-HP. In another example, a cell-free extract which includes an alanine 2,3-aminomutase can be used to form beta-alanine from alpha-alanine. Any method can be used to produce a cell-free extract. For example, osmotic shock, sonication, or a repeated freeze-thaw cycle followed by filtration or centrifugation can be used to produce a cell-free extract from intact cells.

A cell, purified peptide, cell-free extract, or combinations thereof can be used to produce 3-HP that is, in turn, treated chemically to produce another compound. For example, a cell or microorganism can be used to produce 3-HP, while a chemical process is used to modify 3-HP into a derivative such as polymerized 3-HP or an ester of 3-HP. Likewise, a chemical process can be used to produce a particular compound that is, in turn, converted into 3-HP or other organic compound (such as esters of 3-HP, and polymerized 3-HP) using a cell, substantially pure peptide, or cell-free extract described herein.

Fermentation of Cells to Produce Organic Acids

A method is provided for producing 3-HP, derivatives thereof, or both, by culturing production cells, such as a microorganism, in culture medium such that 3-HP, derivatives of 3-HP, or both, are produced. In general, the culture media and culture conditions can be such that the cells grow to an adequate density and produce the product efficiently. For large-scale production processes, any method can be used such as those described elsewhere (Manual of Industrial Microbiology and Biotechnology, $2^{nd}$ Edition, Editors: Demain and Davies, ASM Press; and Principles of Fermentation Technology, Stanbury and Whitaker, Pergamon).

Briefly, a large tank (such as a 100 gallon, 200 gallon, 500 gallon, or more tank) containing appropriate culture medium with, for example, a glucose carbon source is inoculated with a particular cell or microorganism. After inoculation, the cells or microorganisms are incubated to allow biomass to be produced. Once a desired biomass is reached, the broth containing the cells or microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose.

Once transferred, the cells or microorganisms can be incubated to allow for the production of 3-HP, derivatives thereof, or both. Once produced, any method can be used to isolate the formed product. For example, common separation techniques can be used to remove the biomass from the broth, and common isolation procedures (such as extraction, distillation, and ion-exchange procedures) can be used to obtain the 3-HP or derivatives thereof from the cell-free broth. Alternatively, the product can be isolated while it is being produced, or it can be isolated from the broth after the product production phase has been terminated.

Example 1

Construction of *E. coli* Deletion Strains

This example describes methods used to generate *E. coli* hosts for the cloning and expression of beta-alanine/pyruvate aminotransferase and other genes. *E. coli* bacteria were obtained from commercial sources where noted, or constructed by the gene insertional inactivation method of Datsenko and Wanner (*Proc. Natl. Acad. Sci. USA* 97: 6640-5, 2000) using *E. coli* strains BW25113/pKD46 and BW 25141/pKD3 (*E. Coli* Genetic Stock Center, New Haven, Conn.).

Lactate dehydrogenase catalyzes the formation of lactic acid. Deletion of this gene, and hence elimination of lactic acid formation, is advantageous for the detection of the formation of 3-HP because of the similarity in structure and chromatographic behavior of these two compounds. The ΔldhA::cam strain, which has an insertion of a chloramphenicol resistance marker gene into the ldhA locus, was constructed as follows.

The CAT gene conferring chloramphenicol resistance of pKD3 from BW 25141/pKD3 was PCR amplified using: 5'-ATATTTTTAGTAGCTTAAATGTGATTCAACATCACTG-GAGGTGTAGGCTGGAGCTGCTTC (SEQ ID NO: 1), and 5'-TATCTGAATCAGCTCCCCTGGAATGCAGGGG-AGCGGCAAGCATATGAATATCCTCCTTAG (SEQ ID NO: 2), where the underlined portion corresponds to the regions in the E. coli chromosome immediately upstream and downstream of the ldhA locus, respectively, and the non-underlined regions are homologous to regions in pKD3 that permit amplification of a fragment containing the CAT gene.

The PCR reaction contained 30 µl 10× concentrated PCR buffer (Roche Diagnostics, Indianapolis Ind.), approximately 100 ng plasmid pKD3, 0.2 mM each dNTP, 0.2 µM each SEQ ID NO: 1 and 2, and 15 units Taq polymerase (Roche Diagnostics) in a final volume of 300 µl. The PCR reaction was incubated at 95° C. for 30 seconds followed by 30 cycles of 95° C. for 30 seconds, 45° C. for 30 seconds, and 72° C. for 1 minute, then held at 72° C. for 10 minutes. The PCR product was precipitated with ethanol, digested with DpnI (New England Biolabs, Beverly Mass.) purified with the QIAquick PCR Purification Kit (Qiagen, Valencia Calif.), and transformed into BW25113/pKD46 expressing the recombination functions. Transformants were plated on LB plates containing 25 µg/ml chloramphenicol. Chloramphenicol-resistant transformations were single-colony purified on non-selective LB medium at 42° C., and single colonies tested for retention of chloramphenicol resistance and loss of ampicillin resistance (indicating curing of pKD46). Confirmation of correct insertion of the CAT gene into the ldhA locus was performed using colony PCR of the resultant ΔldhA::cam strain using primers that flank the insertion locus:

```
5'-TTCAATATCGCCATAGCTTTCA;      (SEQ ID NO: 3)
and

5'-GAGGATGAAAGGTCATTGG.         (SEQ ID NO: 4)
```

Whereas the wild-type ldhA locus is expected to yield a PCR product of 1112 basepairs (bp) which does not possess a PvuII restriction endonuclease site, the ΔldhA::cam construct yielded a 1161-basepair product which is digested by PvuII to yield fragments of 709 and 452 basepairs, thus confirming the insertion of the CAT gene into the ldhA locus and disruption of the ldhA gene. Electrocompetent cells of E. coli ΔldhA::cam or of other E. coli strains were generated and transformed using standard methods, for example as described in Sambrook et al. Molecular Cloning: A Laboratory Manual, Cold Spring Harbor, N.Y., 1989.

Deletions in the panD, yea, panC, and gabT genes were generated using similar methods. Where necessary, the inserted chloramphenicol resistance marker gene was removed by the activity of the FLP recombinase encoded by plasmid pCP20, as described in Datsenko and Wanner (Proc. Natl. Acad. Sci. USA 97: 6640-5, 2000). For example, a derivative of the ΔpanD::cam strain in which the inserted chloramphenicol resistance marker gene is removed was constructed; the genetic alteration in this strain is referred to as ΔpanD. Deletions were made separately in E. coli BW 25113 and combined by P1 transduction. The strain carrying the combination of ΔpanD, ΔyeiA, ΔpanC, ΔyfdE, and Δ(ygaF-gabD-gabT) is referred to as Car24, and the strain referred to as Car27 contains the deletions carried in Car24 plus ΔldhA::cam.

Example 2

Cloning a Pseudomonas aeruginosa Beta-Alanine/Pyruvate Aminotransferase

The complete amino acid sequence of a protein with beta-alanine/pyruvate aminotransferase activity from Pseudomonas putida IFO 14796 is publicly available (GenBank Accession No. P28269; Yonaha et al., J. Biol. Chem. 267:12506-10, 1992). Waters and Venables (FEMS Microbiol. Letts. 34:279-82, 1986) describe the presence of this activity in P. aeruginosa PAO1, but do not disclose the sequence. Using the BLAST program to identify genes in the P. aeruginosa PAO1 genome that are homologous to the P. putida beta-alanine/pyruvate aminotransferase sequence, GenBank Accession No. NP_248822 was identified as a potential beta-alanine/pyruvate aminotransferase homolog. Primers were designed to amplify this gene based on the complete P. aeruginosa genome (GenBank Accession No. AE004091). The PCR primers used were: 5'-AAGCCCGAGGATCGA CATATGAACCAGCCGCTC (SEQ ID NO: 5) and 5'-CCACCTGCACGGTGGGTACGGC (SEQ ID NO: 6).

The PCR reaction (100 µl total volume) contained 1 µg template DNA (P. aeruginosa PAO1-LAC genomic DNA; American Type Culture Collection, Manassas, Va.; catalog No. 47085D), 0.2 µM each primer (SEQ ID NOS: 5 and 6), 10 µl 10× Taq polymerase buffer (Roche Diagnostics), 0.2 mM each nucleotide triphosphate, and 5 units Taq DNA polymerase (Roche Diagnostics). The mixture was heated at 95° C. for 3 minutes, then subjected to 30 cycles of 95° C. for 30 seconds, 55° C. for 30 seconds, and 72° C. for 90 seconds, and then held at 72° C. for an additional 7 minutes. The reaction was purified with the QIAquick PCR Purification Kit (Qiagen), ethanol-precipitated in the presence of 3 µl Pellet Paint Co-Precipitant (Novagen, Madison, Wis.), treated with NdeI and NotI (New England Biolabs, Beverly, Mass.), purified, and ligated with the Quick Ligation Kit (New England Biolabs) into pPRONde similarly treated with these restriction endonucleases.

The NdeI recognition site (underlined in SEQ ID NO: 5) was generated at the 5' end of the P. aeruginosa beta-alanine/pyruvate aminotransferase gene by the primer of SEQ ID NO: 5, while the NotI site occurs naturally starting 3 nucleotides past (3' of) the termination codon of this gene. Plasmid pPRONde is a derivative of pPROLar.A122 (Clontech Laboratories, Palo Alto, Calif.) in which an NdeI site was constructed at the initiator ATG codon by oligonucleotide-directed mutagenesis using the QuikChange Site-Directed Mutagenesis kit (Stratagene, La Jolla Calif.). Expression of beta-alanine/pyruvate aminotransferase in pPRONde is driven by a hybrid lac/ara promoter. Ligations were transformed into electrocompetent E. coli and clones verified by sequencing. The plasmid carrying the P. aeruginosa beta-alanine/pyruvate aminotransferase gene is referred to herein as pPRO-PaBAPAT.

The cloned P. aeruginosa beta-alanine/pyruvate aminotransferase DNA is shown in SEQ ID NO: 19, and the corresponding protein in SEQ ID NO: 20.

Example 3

Cloning a P. putida Beta-Alanine/Pyruvate Aminotransferase

While the genome sequence of P. putida IFO 14796 has not been determined, the genome sequence of P. putida KT2440, and that of its beta-alanine/pyruvate aminotransferase homolog, is available (Genbank Accession No.

NC_002947.3). PCR primers were designed to amplify this gene from *P. putida* genomic DNA (American Type Culture Collection 47054D) in a manner similar to that used in Example 2: 5'-TCTTCCGAGGAACCGCATATGAACA-TGCCCGAAAC (SEQ ID NO: 7) and 5'-GCATACGCCTG-GCATTAATTAAGGAAAGATCAGTCGATCAG (SEQ ID NO: 8).

NdeI and PacI (underlined sequences in SEQ ID NOS: 7 and 8) were used to clone the PCR product into pPRONde as described in Example 2. The plasmid carrying the *P. putida* beta-alanine/pyruvate aminotransferase gene is referred to as pPRO-PpBAPAT. The cloned *P. putida* beta-alanine/pyruvate aminotransferase cDNA is shown in SEQ ID NO: 17, and the corresponding protein in SEQ ID NO: 18.

One skilled in the art will understand that similar methods can be used to clone a beta-alanine/pyruvate aminotransferase from other organisms, such as *Streptomyces coelicolor* A3, *Corynebacterium glutamicum* ATCC 13032, and rat.

Example 4

Formation of 3-HP from Beta-Alanine Using BAPAT

*E. coli* BW25113 ΔldhA::cam cells carrying pPRONde or pPRO-PaBAPAT (Example 2) were grown in defined minimal medium (Neidhardt et al., *J. Bacteriol.* 119:736-47, 1974) plus 0.4% (w/v) glucose, 20 µg/ml pantothenate, and 25 µg/ml kanamycin at 37° C. to mid-log phase, and expression of beta-alanine/pyruvate aminotransferase induced with 1 mM IPTG. Beta-alanine (50 mM final concentration) was added 50 minutes following induction, and the culture centrifuged after 4 hours to separate the cells from the medium. Samples of the culture supernatant (1 ml) were adjusted to ~pH 2 with 50 µL formic acid, filtered, and 3-HP quantitated by HPLC followed by detection by mass spectrometry.

Chromatography was performed on a Waters 2690 liquid chromatography system using a 2.1 mm×250 mm Phenomenex Aqua $C_{18}$ reversed-phase chromatography column with isocratic elution at 45° C. using 1% methanol:aqueous containing 0.1% (v/v) formic acid as the mobile phase at a flow rate of 0.18 ml/min. Parameters for the Micromass ZQ quadrupole mass spectrometer operating in negative electrospray ionization mode (−ESI) were set as the following; capillary: 2.0 kV; cone: 25 V; extractor: 4 V; RF lens: 1 V; source temperature: 120° C.; desolvation temperature: 380° C.; desolvation gas: 600 L/h; cone gas: Off; low mass resolution: 15.0; high mass resolution: 15.0; ion energy: 0.2; multiplier: 650. A selected ion monitoring MS parameter was set up to allow selection of m/z 89, corresponding to the deprotonated molecular ion, [M-H]−, of 3-HP.

Cells carrying pPRONde did not produce 3-HP, whereas cells carrying pPRO-PaBAPAT produced 0.04 g/L 3-HP. Increasing the incubation time to 20 hours resulted in the formation of 0.06 g/L 3-HP. No 3-HP was produced in the absence of added beta-alanine.

Cells carrying pPRO-PpBAPAT, under the same conditions as those carrying pPRO-PaBAPAT, formed 0.10 g/L 3-HP in 20 hours. Increasing the concentration of supplied beta-alanine to 250 mM in the medium resulted in the formation of 0.24 g/L 3-HP in 20 hours.

Example 5

Synthetic Operon BAPAT-mmsB for 3-HP Production

This example describes methods used to produce an operon that includes a beta-alanine/pyruvate aminotransferase gene and a 3-hydroxyisobutyrate dehydrogenase (mmsB) gene encoding an enzyme with 3-hydroxypropionate dehydrogenase activity. Operons are configurations of genes that are transcribed in tandem as a single messenger RNA. Thus placing genes in close proximity, for example in a plasmid vector, under the transcriptional regulation of a single promoter, constitutes a synthetic operon.

Biosynthetic pathways that allow production of 3-HP via beta-alanine and pyruvate were generated (FIG. 1). One pathway to 3-HP from beta-alanine involves the use of a peptide having beta-alanine/pyruvate aminotransferase activity (EC 2.6.1.18), that is, an enzyme from a class of enzymes that convert beta-alanine to malonate semialdehyde, in addition to an enzyme having 3-HP dehydrogenase activity (E.C. 1.1.1.59), such as that encoded by a mmsB gene (such as SEQ ID NO: 27).

A synthetic operon that includes a beta-alanine/pyruvate aminotransferase gene and a mmsB gene was generated as follows. A mmsB gene was isolated from *P. aeruginosa* 633 genomic DNA (American Type Culture Collection, 17933D) by PCR with primers: 5'-ATACATATGACCGACATCGCAT-TCCTC (SEQ ID NO: 9) and 5'-ATAGTCGACTTAGGGAT-GAAGCAGTGAG (SEQ ID NO: 10).

The DNA polymerase used was a mixture of rTth (1 U; Applied Biosystems) and Pfu (0.125 U, Stratagene, La Jolla Calif.), with the following PCR amplification program: 94° C. for 5 minutes, 25 cycles of 94° C. for 30 seconds, 45° C. (increasing 0.3° C. per cycle) for 30 seconds, and 72° C. for 1 minute (increasing 2 seconds per cycle), followed by 72° C. for 7 minutes. The PCR product was purified using the QIAquick PCR purification kit (Qiagen) then digested with NdeI and SalI (New England Biolabs). The resulting ~1 kb fragment was gel purified using the QIAquick gel purification kit (Qiagen), and ligated into pET28a (Novagen, Madison Wis.) that had been similarly digested and purified. The ligation reaction was done with the Rapid Ligation kit (Roche. Applied Science), and transformed into TOP10 competent cells (Invitrogen, Carlsbad Calif.). The resultant plasmid is denoted pET28-mmsB.

The mmsB gene was amplified from pET28-mmsB using primers: 5'-CAACGGCATCGCCTAATGAACGGCCGCT-TAATTAAGAAGGAGGTASTAAATATGACCGACATCG (SEQ ID NO: 11) and 5'-TTCGTTTTATTTGATGCCTCTA-GATTAGTCCTTGCCGCGGTAGAGC (SEQ ID NO: 12).

The DNA polymerase used was cloned Pfu Turbo DNA pol (Stratagene) with the following PCR amplification program: 95° C. for 30 seconds, 30 cycles of 95° C. for 30 seconds, 60° C. for 30 seconds, and 72° C. for 3 minutes, followed by 72° C. for 10 minutes. The PCR reaction was digested with DpnI and the product gel-purified as above. The fragment was then used as a "mega-primer" in a QuikChange (Stratagene) extension reaction as described by Kirsch and Joly (*Nucl. Acids Res.* 26:1848-50, 1998), using pPRO-PaBAPAT as template. The resultant plasmid carrying a *P. aeruginosa* beta-alanine/pyruvate aminotransferase and an mmsB gene in tandem under the expression control of the $P_{lac/ara}$ promoter is referred to as pBm1. The cloned mmsB cDNA sequence is shown in SEQ ID NO: 27, and the corresponding amino acid sequence in SEQ ID NO: 28.

Cells carrying pBm1 formed 0.09 g/L 3-HP when grown, expressed, and the culture medium analyzed as described in Example 4. These cells were deposited with the American Type Culture Collection (Manassas, Va.) on Dec. 6, 2004 (Accession No. PTA-6411).

Example 6

Synthetic Operon aam-BAPAT-mmsB for 3-HP Production

This example describes methods used to produce an operon that includes a beta-alanine/pyruvate aminotransferase gene, an mmsB gene, as well as an alanine 2,3-aminomutase (aam) gene.

As shown in FIG. 1, beta-alanine can be produced from alpha-alanine by using an alanine 2,3-aminomutase. The alanine 2,3-aminomutase gene used was derived from a *Bacillus subtilis* lysine 2,3-aminomutase by mutagenesis and selection (see WO 03/062173), and included in addition a change of tyrosine at amino acid position 140 to histidine (Y140H) (Bsaam2co, SEQ ID NO. 21). However, one skilled in the art will recognize that other alanine 2,3-aminomutase genes can be used. For example, alternative alanine 2,3-aminomutase gene sequences include, but are not limited to, SEQ ID NOS: 23 and 25 as well as variants, fragments and fusions thereof that retain alanine 2,3-aminomutase activity.

The Bsaam2co alanine 2,3-aminomutase gene carried on a pPROLar-based plasmid was amplified using: 5'-GAG-CAATCACCTATGAACTG (SEQ ID NO: 13) and 5'-GAGCGGCTGGTTCATTTGTACCTTCCTC-CTCTTTAATGGCGGCCGCACCATTCGC ATGTTTT-TATGAAGAATCCC (SEQ ID NO: 14).

The DNA polymerase used was cloned Pfu Turbo DNA pol, with the following PCR amplification program: 95° C. for 30 seconds, 30 cycles of 95° C. for 30 seconds, 54° C. for 30 seconds, and 72° C. for 4 minutes, followed by 72° C. for 20 minutes. The PCR reaction was digested with DpnI and the product gel-purified as above. The fragment was then used as "mega-primer" in a QuikChange extension reaction as described above, using pBm1 as template. The resultant plasmid carrying the alanine 2,3-aminomutase, the *P. aeruginosa* beta-alanine/pyruvate aminotransferase, and the mmsB genes (see Example 5) in tandem under the expression control of the $P_{lac/ara}$ promoter is referred to as pABm1.

A second operon including an alanine 2,3-aminomutase, a *P. putida* beta-alanine/pyruvate aminotransferase (see Example 3), and an mmsB gene in tandem under the expression control of the $P_{lac/ara}$ promoter was constructed. The *P. putida* BAPAT gene was amplified from pPRO-PpBAPAT using primers: 5'-CACACAGAATGCGGCCGCGAG-GAGAAAGGTAAATATGAACATGCCCG (SEQ ID NO: 15) and 5'-CGTTCACCGACAAACAACAG (SEQ ID NO: 16).

The DNA polymerase used was cloned Pfu Turbo DNA pol with the following PCR amplification program: 95° C. for 2 minutes, 30 cycles of 95° C. for 30 seconds, 55° C. for 30 seconds, and 72° C. for 2 minutes, followed by 72° C. for 10 minutes. The PCR product was purified using the QIAquick PCR purification kit (Qiagen), digested with NotI and PacI (New England Biolabs), the 1.4 kb fragment was gel purified and recovered using the QIAquick gel purification kit (Qiagen), and ligated into pABm1 similarly digested and purified. The resultant plasmid carrying alanine 2,3-aminomutase, *P. putida* beta-alanine/pyruvate aminotransferase, and mmsB in tandem under the expression control of the $P_{lac/ara}$ promoter is referred to as pABm2.

Example 7

Expression, Purification, and Assay of *P. putida* BAPAT Activity

The *P. putida* BAPAT cDNA cloned in Example 3 (SEQ ID NO: 17) was subcloned from pPRO-PpBAPAT into pET-28b (Novagen, Madison Wis.) at the NdeI site to generate a protein with an additional 20 amino acids, including a $His_6$ purification tag, at the amino terminus. The subsequent plasmid, pET-PpBAPAT, was transformed into *E. coli* BL21 (DE3) (Novagen) and protein production induced with 0.4 mM IPTG. Cells were disrupted with Bugbuster (5 ml/g wet weight; Novagen) containing rLysozyme (3 KU/ml; Novagen) and Benzonase (25 KU/ml; Novagen), and the cell-free extract applied to His.Bind columns and the His6-BAPAT purified according to the manufacturer's instructions (Novagen).

The assay for BAPAT activity was performed by coupling the production of malonate semialdehyde to its reduction by a NADPH-dependent 3-HP dehydrogenase. The 3-HP dehydrogenase used was the product of the *E. coli* ydfG gene (Fujisawa et al., *Biochim. Biophys. Acta* 1645:89-94, 2003). The assays were performed at 25° C. in 200 μl reactions containing 50 mM K phosphate buffer (pH 8.0), 0.1 mM pyridoxal phosphate, 20 mM β-alanine, 7.5 mM pyruvate, 1 mM NADPH, 0.5 Units of 3-HP dehydrogenase, and purified $His_6$-BAPAT.

Enzymatic activity was monitored as the decrease in $A_{340}$ due to the oxidation of NADPH. The concentrations of β-alanine and pyruvate were varied to determine the $K_m$ for each substrate. Under these conditions, the $K_m$ for β-alanine was 2.2 mM, and that for pyruvate was 1.2 mM. The specific activity of $His_6$-BAPAT was 3.9 Units/mg protein (1 Unit=1 μmol malonate semialdehyde produced per minute).

Example 8

Recombinant Expression

With publicly available enzyme cDNA and amino acid sequences, and the enzymes and sequences disclosed herein, such as beta-alanine/pyruvate aminotransferase, dehydrogenases such as 3-hydroxypropionate dehydrogenase, alanine 2,3-aminomutase, lipase or esterase, alcohol dehydrogenase, and aldehyde dehydrogenase, as well as variants, polymorphisms, mutants, fragments and fusions thereof, the expression and purification of any protein by standard laboratory techniques is enabled. One skilled in the art will understand that enzymes and fragments thereof can be produced recombinantly in any cell or organism of interest, and purified prior to use, for example prior to production of 3-HP and derivatives thereof.

Methods for producing recombinant proteins are well known in the art. Therefore, the scope of this disclosure includes recombinant expression of any protein or fragment thereof, such as an enzyme. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989; Ch. 17).

Briefly, partial, full-length, or variant cDNA sequences that encode for a peptide can be ligated into an expression vector, such as a bacterial expression vector. Proteins peptides can be produced by placing a promoter upstream of the cDNA sequence. Examples of promoters include, but are not limited to lac, trp, tac, trc, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Vectors suitable for the production of intact native proteins include pKC30 (Shimatake and Rosenberg, 1981, *Nature* 292:128), pKK177-3 (Amann and Brosius, 1985, *Gene* 40:183) and pET-3 (Studier and Moffatt, 1986, *J. Mol. Biol.* 189:113). A DNA sequence can be transferred to other cloning vehicles, such as other plasmids, bacteriophages, cosmids, animal viruses and yeast artificial chromosomes (YACs) (Burke et al., 1987, *Science* 236:806-12). These vectors can be introduced into a variety of hosts including somatic cells, and simple or complex organisms, such as bacteria, fungi (Timberlake and Marshall, 1989, *Science* 244: 1313-7), invertebrates, plants (Gasser and Fraley, 1989, *Science* 244:1293), and mammals (Pursel et al., 1989, *Science* 244:1281-8), which are rendered transgenic by the introduction of the heterologous cDNA.

For expression in mammalian cells, a cDNA sequence can be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, 1981, *Cell* 23:175-82), to achieve transient or long-term expression. The stable integration of the chimeric gene construct may be maintained in mammalian cells by biochemical selection, such as neomycin (Southern and Berg, 1982, *J. Mol. Appl. Genet.* 1:327-41) and mycophoenolic acid (Mulligan and Berg, 1981, *Proc. Natl. Acad. Sci. USA* 78:2072-6).

The transfer of DNA into eukaryotic, such as yeast and mammalian cells, is a conventional technique. The vectors are introduced into the recipient cells as pure DNA (transfection) by, for example, precipitation with calcium phosphate (Graham and vander Eb, 1973, *Virology* 52:466) strontium phosphate (Brash et al., 1987, *Mol. Cell. Biol.* 7:2013), electroporation (Neumann et al., 1982, *EMBO J.* 1:841), lipofection (Felgner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors, for example retroviruses (Bernstein et al., 1985, *Gen. Engrg.* 7:235) such as adenoviruses (Ahmad et al., 1986, *J. Virol.* 57:267) or Herpes (Spaete et al., 1982, *Cell* 30:295).

In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A transformed prokaryotic cell comprising:
    an exogenous nucleic acid molecule encoding a beta-alanine/pyruvate aminotransferase having at least 95% sequence identity to SEQ ID NO: 20, wherein the beta-alanine/pyruvate aminotransferase is capable of producing malonate semialdehyde and alanine from beta-alanine and pyruvate, and
    an exogenous nucleic acid molecule encoding an alanine 2,3-aminomutase, wherein the alanine 2,3-aminomutase is capable of producing beta-alanine from alpha-alanine, wherein the prokaryotic cell produces 3-hydroxypropionic acid (3-HP) from beta-alanine.

2. The transformed cell of claim 1, wherein the exogenous nucleic acid molecule encoding the beta-alanine/pyruvate aminotransferase comprises a sequence having at least 95% sequence identity to SEQ ID NO: 19.

3. The transformed cell of claim 1, wherein the exogenous nucleic acid molecule encoding the beta-alanine/pyruvate aminotransferase comprises SEQ ID NO: 19.

4. The transformed cell of claim 1, wherein the cell further comprises dehydrogenase activity capable of converting malonate semialdehyde to 3-HP.

5. The transformed cell of claim 4, wherein the cell further comprises an exogenous nucleic acid molecule encoding a dehydrogenase capable of converting malonate semialdehyde to 3-HP.

6. The transformed cell of claim 5, wherein the dehydrogenase is a 3-hydroxypropionate dehydrogenase.

7. The transformed cell of claim 6, wherein the exogenous nucleic acid molecule encoding the 3-hydroxypropionate dehydrogenase comprises a sequence having at least 95% sequence identity to SEQ ID NO: 27.

8. The transformed cell of claim 7, wherein the exogenous nucleic acid molecule encoding the 3-hydroxypropionate dehydrogenase comprises SEQ ID NO: 27.

9. The transformed cell of claim 6, wherein the 3-hydroxypropionate dehydrogenase comprises SEQ ID NO: 28.

10. The transformed cell of claim 1, wherein the exogenous nucleic acid molecule that encodes an alanine 2,3-aminomutase comprises a sequence having at least 95% sequence identity to SEQ ID NO: 25 and the alanine 2,3-aminomutase is capable of producing beta-alanine from alpha-alanine.

11. The transformed cell of claim 10, wherein the exogenous nucleic acid molecule that encodes an alanine 2,3-aminomutase comprises SEQ ID NO: 25.

12. The transformed cell of claim 1, wherein the alanine 2,3-aminomutase comprises SEQ ID NO: 26.

13. The transformed cell of claim 1, wherein the prokaryotic cell is a *Lactobacillus, Lactococcus, Bacillus*, or *Escherichia* cell.

14. The transformed cell of claim 1, wherein the cell further comprises lipase or esterase activity, or a combination thereof.

15. The transformed cell of claim 14, wherein the cell further comprises an exogenous nucleic acid molecule encoding a lipase or an esterase.

16. The transformed cell of claim 1, wherein the cell further comprises:
3-hydroxypropionate dehydrogenase activity and lipase or esterase activity.

17. The transformed cell of claim 14, wherein the transformed cell produces an ester of 3-HP.

18. The cell of claim 17, wherein the ester of 3-HP is methyl 3-hydroxypropionate, ethyl 3-hydroxypropionate, propyl 3-hydroxypropionate, butyl 3-hydroxypropionate, or 2-ethylhexyl 3-hydroxypropionate.

19. The transformed cell of claim 1, wherein the cell further comprises aldehyde dehydrogenase activity and alcohol dehydrogenase activity.

20. The transformed cell of claim 19 wherein the cell further comprises an exogenous nucleic acid molecule encoding an aldehyde dehydrogenase and an exogenous nucleic acid molecule encoding an alcohol dehydrogenase.

21. The transformed cell of claim 1, wherein the cell further comprises:
3-hydroxypropionate dehydrogenase activity;
aldehyde dehydrogenase activity; and
alcohol dehydrogenase activity.

22. The transformed cell of claim 19, wherein the transformed cell produces 1,3-propanediol.

23. The transformed cell of claim 1, wherein the cell further comprises esterase activity.

24. The transformed cell of claim 23, wherein the cell further comprises an exogenous nucleic acid molecule encoding an esterase.

25. The transformed cell of claim 1, wherein the cell further comprises:
3-hydroxypropionate dehydrogenase activity; and
esterase activity.

26. The transformed cell of claim 23, wherein the transformed cell produces polymerized 3-HP.

27. A method for making 3-HP from beta-alanine, comprising culturing the transformed cell of claim 1 under conditions that allow the transformed cell to make 3-HP from beta-alanine.

28. The method of claim 27, wherein the cell is an *E. coli* cell.

29. A method of producing an ester of 3-HP, comprising culturing the transformed cell of claim 14 under conditions wherein the transformed cell produces an ester of 3-HP.

30. The method of claim 29, wherein the ester of 3-HP is methyl 3-hydroxypropionate, ethyl 3-hydroxypropionate, propyl 3-hydroxypropionate, butyl 3-hydroxypropionate, or 2-ethylhexyl 3-hydroxypropionate.

31. A method of producing 1,3 propanediol, comprising culturing the transformed cell of claim 19 under conditions wherein the transformed cell produces 1,3 propanediol.

32. A method of producing polymerized 3-HP, comprising culturing the transformed cell of claim 23 under conditions wherein the transformed cell produces polymerized 3-HP.

33. A method for making 3-HP, comprising:
culturing the transformed cell of claim 1 to allow the transformed cell to make 3-HP.

34. The transformed cell of claim 1, wherein the alanine 2,3-aminomutase comprises at least 95% sequence identity to SEQ ID NO: 26 and is capable of producing beta-alanine from alpha-alanine.

35. The transformed cell of claim 1, wherein the cell does not express lactate dehydrogenase.

36. The transformed cell of claim 1, wherein the cell is an *E. coli* cell.

37. The transformed cell of claim 1, wherein the exogenous nucleic acid molecule encoding the beta-alanine/pyruvate aminotransferase comprises a sequence that can hybridize under highly stringent hybridization conditions to SEQ ID NO: 19, wherein the highly stringent hybridization conditions comprise incubation at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% dextran sulfate, and 1-15 ng/mL probe and washes are performed at about 65° C. with a wash solution containing 0.2×SSC and 0.1% SDS.

38. The transformed cell of claim 1, wherein the exogenous nucleic acid molecule encoding the alanine 2,3-aminomutase comprises a sequence that can hybridize under highly stringent hybridization conditions to SEQ ID NO: 25, wherein the highly stringent hybridization conditions comprise incubation at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% dextran sulfate, and 1-15 ng/mL probe and washes are performed at about 65° C. with a wash solution containing 0.2×SSC and 0.1% SDS.

* * * * *